(12) United States Patent
Cockerill et al.

(10) Patent No.: US 6,830,888 B2
(45) Date of Patent: Dec. 14, 2004

(54) **DETECTION OF *LEGIONELLA***

(75) Inventors: Franklin R. Cockerill, Rochester, MN (US); Randall T. Hayden, Memphis, TN (US); James R. Uhl, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 47 days.

(21) Appl. No.: 10/140,741

(22) Filed: May 7, 2002

(65) Prior Publication Data

US 2003/0082577 A1 May 1, 2003

Related U.S. Application Data

(60) Provisional application No. 60/289,222, filed on May 7, 2001.

(51) Int. Cl.$^7$ .............................. C12Q 1/68; C12P 19/34; C07H 21/04

(52) U.S. Cl. ..................... 435/6; 435/91.1; 435/91.2; 435/183; 536/24.3; 536/24.32; 536/24.33

(58) Field of Search ........................... 435/6, 91.2, 91.1, 435/183; 536/24.3, 24.32, 24.33; 935/1.8, 76, 77

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,722,891 A | | 2/1988 | Drutz et al. |
| 4,800,159 A | | 1/1989 | Mullis et al. |
| 4,851,333 A | | 7/1989 | Goldstein et al. |
| 4,965,188 A | | 10/1990 | Mullis et al. |
| 4,996,143 A | | 2/1991 | Heller et al. |
| 5,035,996 A | | 7/1991 | Hartley |
| 5,491,225 A | * | 2/1996 | Picone et al. ............ 536/24.32 |
| 5,565,322 A | | 10/1996 | Heller |
| 5,569,586 A | | 10/1996 | Pelletier et al. |
| 5,614,388 A | | 3/1997 | Picone et al. |
| 5,674,684 A | | 10/1997 | Hogan et al. |
| 5,677,127 A | | 10/1997 | Hogan et al. |
| 5,677,128 A | | 10/1997 | Hogan et al. |
| 5,677,129 A | | 10/1997 | Hogan et al. |
| 5,683,896 A | | 11/1997 | Hartley et al. |
| 5,827,651 A | | 10/1998 | Hogan et al. |
| 5,840,488 A | | 11/1998 | Hogan |
| 5,849,489 A | | 12/1998 | Heller |
| 5,945,313 A | | 8/1999 | Hartley et al. |
| 5,958,679 A | | 9/1999 | Hogan et al. |
| 5,968,739 A | * | 10/1999 | Macioszek et al. ............ 435/6 |
| 5,994,059 A | | 11/1999 | Hogan et al. |
| 6,162,603 A | | 12/2000 | Heller |
| 6,251,609 B1 | | 6/2001 | Brink et al. |
| 6,287,781 B1 | * | 9/2001 | Lee et al. ...................... 435/6 |
| 2002/0123062 A1 | * | 9/2002 | Whittwer ...................... 435/6 |

FOREIGN PATENT DOCUMENTS

| | | |
|---|---|---|
| EP | 1 045 033 | 10/2000 |
| WO | WO 97/46707 | 12/1997 |
| WO | WO 97/46712 | 12/1997 |
| WO | WO 97/46714 | 12/1997 |
| WO | WO 98/48046 | 10/1998 |

OTHER PUBLICATIONS

MacDonell, M. T. et al "The nucleotide sequence of the 5S rRNA from *Legionella pneumophila*" Nucleic Acid Res 15 (3), 1335 (1987).*

Newton PCR Essential Data, John Wiley & Sons Ltd, 1995, pp. 49–56.*

GenBank Accession No. Z30435.

GenBank Accession No. Z30540.

GenBank Accession No. AF095220.

GenBank Accession No. AF095230.

Aebischer et al., "Diagnosis by Polymerase Chain Reaction of Pneumonia Caused by *Legionella pneumophila* in an Immunocompetent Child," *Infection*, 1999, 27(4/5):280–282.

Grimm et al., "Specific Detection of *Legionella pneumophila*: Construction of a New 16S rRNA–Targeted Oligonucleotide Probe," *Appl. Environ. Microbiol.*, 1998, 64(7):2686–2690.

Hayden et al., "Direct Detection of *Legionella* Species From Bonchial Alveolar Lung (BAL) Specimens Using a Rapid PCR Method," *Am. Soc. Microbiol.*, 100$^{th}$ General Meeting, Los Angeles Convention Center, Los Angeles, CA, May 21–25, 2000, p. 171, Abstract C–180.

Hayden et al., "Direct Detection of *Legionella* Species from Bronchoalveolar Lavage and Open Lung Biopsy Specimens: Comparison of LightCycler PCR, In Situ Hybridization, Direct Fluorescence Antigen Detection, and Culture," *J. Clin. Microbiol.*, 2001, 39(7):2618–2626.

Mahbubani et al., "Detection of *Legionella* with polymerase chain reaction and gene probe methods," *Mol. Cell. Probes*, 1990, 4:175–187.

Waterer et al., "*Legionella* and Community–Acquired Pneumonia: A Review of Current Diagnostic Tests from a Clinician'Viewpoint," *Am. J. Med.*, 2001, 110:41–48.

Al–Robaiy et al., "Rapid Competitive PCR Using Melting Curve Analysis for DNA Quantification," *BioTechniques*, 2001, 31:1382–1388.

(List continued on next page.)

*Primary Examiner*—Jezia Riley
(74) *Attorney, Agent, or Firm*—Fish & Richardson P. C., P.A.

(57) ABSTRACT

The invention provides methods to detect *Legionella* and further to detect *L. pneumophila* in biological samples using real-time PCR. Primers and probes for the detection of *Legionella* and *L. pneumophila* are provided by the invention. Articles of manufacture containing such primers and probes for detecting *Legionella* and *L. pneumophila* are further provided by the invention.

93 Claims, No Drawings

OTHER PUBLICATIONS

Bélanger et al., "Rapid Detection of Shiga Toxin–Producing Bacteria in Feces by Multriplex PCR with Molecular Beacons on the Smart Cycler," *J. Clin. Microbiol.*, 2002, 40:1436–1440.

Bellin et al., "Rapid Detection of Enterohemorrhagic *Escherichia coli* by Real–Time PCR with Fluorescent Hybridization Probes," *J. Clin. Microbiol.*, 2001, 39:370–374.

Chen et al., An Automated Fluorescent PCR Method for Detection of Shiga Toxin–Producing *Escherichia coli* in Foods,: *Appl. Environ. Microbiol.*, 1998, 64:4210–4216.

Didenko, "DNA Probes Using Fluorescence Resonance Energy Transfer (FRET): Designs and Applications," *BioTechniques*, 2001, 31:1106–1121.

Ramotar et al., "Direct Detection of Verotoxin–Producing *Escherichia coli* in Stool Samples by PCR," *J. Clin. Microbiol.*, 1995, 33:519–524.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357–362.

\* cited by examiner

DETECTION OF LEGIONELLA

CROSS REFERENCE TO RELATED APPLICATIONS

This application claims priority under 35 U.S.C. §119(e) of U.S. provisional application Ser. No. 60/289,222, filed May 7, 2001.

TECHNICAL FIELD

This invention relates to bacterial diagnostics, and more particularly to detection of Legionella species, particularly Legionella pneumophila.

BACKGROUND

The genus Legionella, family Legionellaceae, includes over 40 different species of fastidious gram-negative bacilli, with over 60 described serogroups. While some of these organisms represent normal environmental flora, many have been shown to cause human disease, namely opportunistic pneumonia in immunocompromised patients. The vast majority of such cases (approximately 85%) are due to L. pneumophila, with the remainder due to other species, most commonly L. micdadei, L. bozemanii, L. dumoffii, and L. longbeachae. Legionella pneumonia can be community acquired or nosocomial, and sporadic or epidemic in nature. Pulmonary infection may be subclinical, or severe and life threatening. The fatality rate can approach 50% in immunocompromised patients. The organism often responds to antimicrobial therapy, usually with macrolides, and clinical responses usually occur within 3–5 days. The latter fact, combined with clinical and radiographic features that are often non-specific, serve to underscore the value of a prompt and accurate laboratory diagnosis.

SUMMARY

The invention provides for methods of identifying Legionella in a biological sample, and further, for specifically detecting Legionella pneumophila. Primers and probes for detecting Legionella, specifically L. pneumophila, are provided by the invention, as are kits containing such primers and probes. Methods of the invention can be used to rapidly identify Legionella nucleic acids from specimens for diagnosis of Legionella infection. Using specific primers and probes, the methods include amplifying and monitoring the development of specific amplification products using real-time PCR.

In one aspect of the invention, there is provided a method for detecting the presence or absence of Legionella in a biological sample from an individual. The method to detect Legionella includes performing at least one cycling step, which includes an amplifying step and a hybridizing step. The amplifying step includes contacting the sample with a pair of 5S rRNA primers to produce a 5S rRNA amplification product if Legionella nucleic acid encoding 5S rRNA is present in the sample, and the hybridizing step includes contacting the sample with a pair of 5S rRNA probes. Generally, the members of the pair of 5S rRNA probes hybridizes to the amplification product within no more than five nucleotides of each other. A first 5S rRNA probe of the pair of 5 S rRNA probes is typically labeled with a donor fluorescent moiety and a second 5S rRNA probe of the pair of 5S rRNA probes is typically labeled with a corresponding acceptor fluorescent moiety. The method further includes detecting the presence or absence of fluorescent resonance energy transfer (FRET) between the donor fluorescent moiety of the first 5S rRNA probe and the acceptor fluorescent moiety of the second 5S rRNA probe. The presence of FRET is usually indicative of the presence of Legionella in the biological sample, while the absence of FRET is usually indicative of the absence of Legionella in the biological sample. In addition, determining the melting temperature between one or both of the 5S rRNA probe(s) and the corresponding probe targets can confirm the presence or absence of the Legionella.

In another aspect, the invention features a method for detecting the presence or absence of L. pneumophila in a biological sample from an individual. The method to detect L. pneumophila includes performing at least one cycling step, which includes an amplifying step and a hybridizing step. The amplifying step includes contacting the sample with a pair of mip primers to produce a mip amplification product if L. pneumophila nucleic acid encoding mip is present in the sample, and the hybridizing step includes contacting the sample with a pair of mip probes. Generally, the members of the pair of mip probes hybridizes to the amplification product within no more than five nucleotides of each other. A first mip probe of the pair of mip probes is typically labeled with a donor fluorescent moiety and a second mip probe of the pair of mip probes is typically labeled with a corresponding acceptor fluorescent moiety. The method further includes detecting the presence or absence of FRET between the donor fluorescent moiety of the first mip probe and the acceptor fluorescent moiety of the second mip probe. The presence of FRET is usually indicative of the presence of L. pneumophila in the biological sample, while the absence of FRET is usually indicative of the absence of L. pneumophila in the biological sample. The method to detect L. pneumophila can be performed after the method has been performed to detect Legionella or concurrent with the method to detect Legionella.

A pair of 5S rRNA primers generally includes a first 5S rRNA primer and a second 5S rRNA primer. The first 5 S rRNA primer can include the sequence 5'-ACT ATA GCG ATT TGG AAC C-3' (SEQ ID NO: 1), and the second 5S rRNA primer can include the sequence 5'-GGC GAT GAC CTA CTT TC-3' (SEQ ID NO:2). The first 5S rRNA probe can include the sequence 5'-CAT GAG GAA GCC TCA CAC TAT CA-3' (SEQ ID NO:3), and the second 5S rRNA probe can include the sequence 5'-GGC GAT GAC CTA CTT TC-3' (SEQ ID NO:2). In certain aspects, the second 5S rRNA primer can be labeled with a donor fluorescent moiety and can act as the second 5S rRNA probe.

A pair of mip primers generally includes a first mip primer and a second mip primer. The first mip primer can include the sequence 5'-ACC GAA CAG CAA ATG AAA GA-3' (SEQ ID NO:4), and the second mip primer can include the sequence 5'-AAC GCC TGG CTT GTT TTT GT-3' (SEQ ID NO:5). The first mip probe can include the sequence 5'-AAC AAG TTT CAG AAA GAT TTG ATG GCA AAG-3' (SEQ ID NO:6), and the second mip probe can include the sequence 5'-GTA CTG CTG AAT TCA ATA AGT AAG CGG ATG-3' (SEQ ID NO:7).

The members of the pair of 5S rRNA probes can hybridize within no more than two nucleotides of each other, or can hybridize within no more than one nucleotide of each other. A representative donor fluorescent moiety is fluorescein, and representative acceptor fluorescent moieties include LC™-RED 640 (LightCycler™-Red 640-N-hydroxysuccinimide ester), LC™-RED 705 (LightCycler™-Red 705-Phosphoramidite), and cyanine dyes such as CY5 and CY5.5.

In one aspect, the detecting step includes exciting the biological sample at a wavelength absorbed by the donor fluorescent moiety and visualizing and/or measuring the wavelength emitted by the acceptor fluorescent moiety. In another aspect, the detecting includes quantitating the FRET. In yet another aspect, the detecting step is performed after each cycling step, and further, can be performed in real-time.

Generally, the presence of the FRET in an amount at least 3 times the amount of FRET in a sample lacking the *Legionella* 5S rRNA nucleic acid molecule indicates the presence of a *Legionella* infection in the individual. Representative biological sample include sputum, bronchioalveolar lavage, bronchial aspirates, lung tissue, urine and blood.

The above-described methods can further include preventing amplification of a contaminant nucleic acid. Preventing amplification can include performing the amplifying step in the presence of uracil and treating the biological sample with uracil-DNA glycosylase prior to a first amplification step. In addition, the cycling step can be performed on a control sample. A control sample can include a portion of the *Legionella* nucleic acid molecule encoding 5S rRNA. Alternatively, such a control sample can be amplified using a pair of control primers and hybridized using a pair of control probes. The control primers and the control probes are usually other than the 5S rRNA primers and 5S rRNA probes, respectively. A control amplification product is produced if control template is present in the sample, and the control probes hybridize to the control amplification product.

In another aspect of the invention, there are provided articles of manufacture, including a pair of 5S rRNA primers; a pair of 5S rRNA probes; and a donor fluorescent moiety and a corresponding fluorescent moiety. A pair of 5S rRNA primers generally includes a first 5S rRNA primer and a second 5S rRNA primer. The first 5S rRNA primer can include the sequence 5'-ACT ATA GCG ATT TGG AAC C-3' (SEQ ID NO:1), and the second 5S rRNA primer can include the sequence 5'-GGC GAT GAC CTA CTT TC-3' (SEQ ID NO:2). A pair of 5S rRNA probes generally includes a first 5S rRNA probe and a second 5S rRNA probe. The first 5S rRNA probe can include the sequence 5'-CAT GAG GAA GCC TCA CAC TAT CA-3' (SEQ ID NO:3), and the second 5S rRNA probe can include the sequence 5'-GGC GAT GAC CTA CTT TC-3' (SEQ ID NO:2). Articles of manufacture of the invention can further or alternatively include a pair of mip primers; a pair of mip probes; and a donor fluorescent moiety and a corresponding fluorescent moiety. A pair of mip primers generally includes a first mip primer and a second mip primer. The first mip primer can include the sequence 5'-ACC GAA CAG CAA ATG AAA GA-3' (SEQ ID NO:4), and the second mip primer can include the sequence 5'-AAC GCC TGG CTT GTT TTT GT-3' (SEQ ID NO:5). A pair of mip probes generally includes a first mip probe and a second mip probe. The first mip probe can include the sequence 5'-AAC AAG TTT CAG AAA GAT TTG ATG GCA AAG-3' (SEQ ID NO:6), and the second mip probe can include the sequence 5'-GTA CTG CTG AAT TCA ATA AGT AAG CGG ATG-3' (SEQ ID NO:7). The probes in such articles of manufacture can be labeled with a donor fluorescent moiety and with a corresponding acceptor fluorescent moiety. The article of manufacture can also include a package label or package insert having instructions thereon for using the pair(s) of primers and pair(s) of probes to detect the presence or absence of *Legionella* or *L. pneumophila* in a biological sample.

In yet another aspect, the invention provides a method for detecting the presence or absence of *Legionella* in a biological sample from an individual. Such a method includes performing at least one cycling step, wherein a cycling step comprises an amplifying step and a hybridizing step. An amplifying step includes contacting the sample with a pair of 5S rRNA primers to produce a 5S rRNA amplification product if a *Legionella* nucleic acid molecule encoding the 5S rRNA is present in the sample. A hybridizing step includes contacting the sample with a 5S rRNA probe, wherein the 5S rRNA probe is labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the 5S rRNA probe. The presence or absence of FRET is indicative of the presence or absence of *Legionella* in the sample. Amplification can employ a polymerase enzyme having 5' to 3' exonuclease activity, and the donor and acceptor fluorescent moieties can be within no more than 5 nucleotides of each other on the probe. In such a method, the 5S rRNA probe can include a nucleic acid sequence that permits secondary structure formation that results in spatial proximity between the donor and the acceptor fluorescent moiety. In the above-described methods, the acceptor fluorescent moiety can be a quencher. A similar method can be used to detect *L. pneumophila* using a pair of mip primers and a mip probe.

In another aspect, the invention provides a method for detecting the presence or absence of *Legionella* in a biological sample from an individual. Such a method includes performing at least one cycling step, wherein a cycling step comprises an amplifying step and a dye-binding step. An amplifying step includes contacting the sample with a pair of 5S rRNA primers to produce a 5S rRNA amplification product if a *Legionella* nucleic acid molecule encoding a 5S rRNA is present in the sample. A dye-binding step comprises contacting the 5S rRNA amplification product with a nucleic acid binding dye. The method further includes detecting the presence or absence of binding of the nucleic acid binding dye to the amplification product. The presence of binding is usually indicative of the presence of *Legionella* in the sample, and the absence of binding is usually indicative of the absence of *Legionella* in the sample. Representative nucleic acid binding dyes include SYBRGREENI®, SYBRGOLD®, and ethidium bromide. Such a method can further include determining the melting temperature between the 5S rRNA amplification product and the nucleic acid binding dye. The melting temperature can confirm the presence or absence of the *Legionella*. Similarly, such a method can be used to specifically detect *L. pneumophila* using a pair of mip primers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

The present invention provides for methods of detecting *Legionella* in a biological sample, and for specifically detecting *L. pneumophila*. Primers and probes for detecting *Legionella* infections in general, or specifically *L. pneumophila* infections, are provided. Articles of manufacture containing such primers and probes also are provided by the invention. With conventional culture serving as the "gold standard," a real-time PCR assay was compared to a direct fluorescent antibody (DFA) assay for the detection of *Legionella* species in BAL specimens, and to a DFA assay, in situ hybridization (ISH), and Warthin Starry (WS) staining for the detection of *Legionella* species in open lung biopsy specimens. The increased sensitivity of real-time PCR compared to other methods, as well as the improved features of real-time PCR including sample containment and real-time detection of the amplified product indicate the feasibility for implementation of this technology for routine diagnosis of *Legionella* infections, specifically those attributable to *L. pneumophila*, in the clinical laboratory.

*Legionella* Species and *L. pneumophila*

Bacteria of the genus *Legionella* are intracellular parasites and major human pathogens. They bind to surface receptors, penetrate eukaryotic cells and initiate complex disorders during phagocytosis. These disorders include inhibition of oxidative burst, a decrease in phagosome acidification, the blocking of phagasome maturation and changes in organelle trafficking. As a result, the microorganisms prevent the bactericidal activity of the phagocyte and transform the phagosome into a niche for their replication. Biological, biochemical and molecular-genetic approaches have been used to identify a panel of bacterial products that may be involved in *Legionella* virulence. They include cytotoxins, several enzymes and a set of genes thought to encode proteins of the export machinery. The interaction of virulent *Legionella* with phagocytic cells can be arbitrarily divided into several steps: binding of microorganisms to receptors on the surface of eukaryotic cells, penetration of microorganisms into phagocytes, escape from bactericidal attack, formation of a replicative vacuole, intracellular multiplication, and killing of the host cell.

In many bacteria, the 16S, 23S, and 5S rRNAs are encoded in unlinked operons approximately 5 kilobases (kb) in length. *E. coli* and *S. typhimurium* have seven rRNA operons. When multiple operons are present, they are organized similarly and have the order 16S, 23S and 5S. Genes for tRNA are generally located between the 16S and 23S rRNA genes and sometimes after the 5S gene. The three mature rRNA sequences are separated by spacer sequences that are removed during processing. The spacer regions are highly conserved between operons. Long inverted repeats, flanking both the 16S and 23S rRNAs, have the potential to form double-stranded stems at the base of the 16S and 23S rRNAs. These double-stranded regions are predicted to be stable in vivo and have been observed directly by electron microscopy. Each operon contains two tandem promoters, one of which is responsive to control by guanosine 5'-diphosphate, 3'-diphosphate (ppGpp), and the other that is subject to growth rate control. Initial cleavages separate 16S and 23S RNA, usually before transcription of the operon is complete.

Mutations in a gene coding for a 24 kDa surface protein of *Legionella* species, as well as other intracellular organisms such as *Chlamydia*, *Coxiella* and *Rickettsia*, result in a severe reduction in virulence towards macrophages, macrophage-like cell lines, alveolar epithelial cells and protozoa. They also cause considerable attenuation of *L. pneumophila* in laboratory animals. As such mutants are impaired in their ability to initiate macrophage infection, the mutated surface component was named the macrophage infectivity potentiator (mip) protein.

The deduced amino acid sequence of the mip protein from *L. pneumophila* shows homology to human, Neurospora and yeast proteins able to bind the immunosupressant drug FK506. FK506-binding proteins are receptors belonging to a family of peptidyl-prolyl cisltrans isomerases (PPIs) called immunophilins, which catalyze the cisltrans interconversion of prolyl imidic peptide bonds in proteins. Investigations with the 24 kDa mip protein confirmed that it has isomerase activity. In addition, the inhibitory effect of FK506 on mip was similar to that on human FK506-binding protein.

The N-terminus of mip, which is predicted to be a 60-amino acid α-helix, apparently anchors the protein to the bacterial cell wall. The C-terminus, which carries a domain possessing peptidyl-prolyl cisltrans isomerase, projects distally from the bacterial surface to accomplish its biological function. Data from an X-ray solution scattering study suggested that the mip protein functions as a dimer.

*Legionella* Nucleic Acids and Oligonucleotides

The invention provides methods to detect *Legionella* by amplifying *Legionella* nucleic acid molecules encoding, for example, a portion of the 5S rRNA. The invention further provides methods to specifically detect *L. pneumophila* by amplifying *L. pneumophila* nucleic acid molecules encoding, for example, mip. *Legionella* and *L. pneumophila*-specific nucleic acid molecules other than those exemplified herein (e.g., those encoding 5S rRNA and mip, respectively) can be used to detect *Legionella* and *L. pneumophila* in a sample and are known to those of skill in the art. Nucleic acid sequences encoding *Legionella* 5S rRNA have been described (see, for example, GenBank Accession Nos. Z30435 or Z30540), as have nucleic acid sequences encoding *L. pneumophila* mip (see, for example, GenBank Accession Nos. AF095230 and AF095220). Specifically, primers and probes to amplify and detect *Legionella* 5S rRNA nucleic acid molecules are provided by the invention. Similarly, primers and probes to amplify and detect *L. pneumophila* mip nucleic acid molecules are also provided by the invention.

Primers that amplify a *Legionella* nucleic acid molecule, e.g., a nucleic acid molecule encoding mip or a portion of the 5S rRNA, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (e.g., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "5S rRNA primers" as used herein refers to oligonucleotide primers that specifically anneal to *Legionella* nucleic acid sequences encoding 5S rRNA and initiate synthesis therefrom under appropriate conditions. Likewise, "mip primers" refers to oligonucleotide primers that specifically anneal to *L. pneumophila* nucleic acid sequences encoding mip and initiate synthesis therefrom under appropriate conditions.

Designing oligonucleotides to be used as hybridization probes can be performed in a manner similar to the design of primers, although the members of a pair of probes preferably hybridize to an amplification product within no more than 5 nucleotides of each other on the same strand such that fluorescent resonance energy transfer (FRET) can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a polymorphism or mutation, thereby allowing differential detection of *Legionella* species or members within a species based on either absolute hybridization of different pairs of probes corresponding to the particular *Legionella* species or member to be distinguished or differential melting temperatures between, for example, members of a pair of probes and each amplification product corresponding to the *Legionella* species or member to be distinguished (e.g., *L. pneumophila* from *L. oakridgenesis*). As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "5S rRNA probes" as used herein refers to oligonucleotide probes that specifically anneal to a 5S rRNA amplification product. Similarly, "mip probes" refers to oligonucleotide probes that specifically anneal to a mip amplification product.

Constructs of the invention include vectors containing *Legionella* nucleic acid molecules or fragments thereof, for example, those encoding 5S rRNA or mip. Constructs can be used, for example, as a control template nucleic acid. Vectors suitable for use in the present invention are commercially available and/or produced by recombinant DNA technology methods routine in the art. A *Legionella* nucleic acid molecule encoding 5S rRNA or mip can be obtained, for example, by chemical synthesis, direct cloning from a *Legionella* species, or by PCR amplification. A *Legionella* 5S rRNA or mip nucleic acid molecule, or fragments thereof, can be operably linked to a promoter or other regulatory element such as an enhancer sequence, a response element, or an inducible element that modulates expression of the 5S rRNA or mip nucleic acid molecule. As used herein, operably linking refers to connecting a promoter and/or other regulatory elements to a *Legionella* nucleic acid encoding a 5S rRNA or mip in such a way as to permit and/or regulate expression of the 5S rRNA or mip nucleic acid molecule. A promoter that does not normally direct expression of a 5S rRNA nucleic acid sequence can be used to direct transcription of a 5S rRNA nucleic acid molecule using, for example, a viral polymerase, a bacterial polymerase, or a eukaryotic RNA polymerase II. Alternatively, the 5S rRNA native "internal" promoter can be used to direct transcription of a 5S rRNA nucleic acid using, for example, an RNA polymerase III enzyme. In addition, operably linked can refer to an appropriate connection between a *Legionella* 5S rRNA or mip promoter or other regulatory element to a heterologous coding sequence (e.g., a non-5S rRNA or non-mip coding sequence, for example, a reporter gene) in such a way as to permit expression of the heterologous coding sequence.

Constructs suitable for use in the methods of the invention typically include, in addition to *Legionella* nucleic acid molecules encoding 5S rRNA or mip, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing *Legionella* nucleic acid molecules encoding 5S rRNA or mip can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two primers that bind to a selected nucleic acid template (e.g., DNA or RNA). Primers useful in the present invention include oligonucleotides capable of acting as a point of initiation of nucleic acid synthesis within the *Legionella* 5S rRNA nucleic acid molecule or *L pneumophila* mip nucleic acid molecule. A primer can be purified from a restriction digest by conventional methods, or it can be produced synthetically. The primer is preferably single-stranded for maximum efficiency in amplification, but a primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length.

If the double-stranded nucleic acid is denatured by heat, the reaction mixture is allowed to cool to a temperature that promotes annealing of each primer to its target sequence on the template nucleic acid. The temperature for annealing is usually from about 35° C. to about 65° C. The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template. The temperature generally ranges from about 40° to 80° C.

PCR assays can employ, for example, DNA or RNA, including messenger RNA (mRNA). The template nucleic acid need not be purified; it may be a minor fraction of a complex mixture, such as *Legionella* nucleic acid contained in human cells. DNA or RNA may be extracted from any biological sample such as sputum, a bronchio-alveolar lavage, bronchial aspirates, lung tissue, urine or blood by routine techniques such as those described in Diagnostic Molecular Microbiology: Principles and Applications (Persing et al. (eds), 1993, American Society for Microbiology, Washington D.C.). Template nucleic acids can be obtained from any number of sources, such as plasmids, or natural sources including bacteria, yeast, viruses, organelles, or higher organisms such as plants or animals.

The oligonucleotide primers are combined with other PCR reagents under reaction conditions that induce primer extension. For example, chain extension reactions generally include 50 mM KCl, 10 mM Tris-HCl (pH 8.3), 1.5 mM $MgCl_2$, 0.001% (w/v) gelatin, 0.5–1.0 $\mu$g denatured template DNA, 50 pmoles of each oligonucleotide primer, 2.5 U of Taq polymerase, and 10% DMSO). The reaction usually contains 150 to 320 $\mu$M each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target *Legionella* nucleic acid molecule. The limiting factors in the reaction are the amounts of primers, thermostable enzyme, and nucleoside triphosphates present in the reaction. The cycling steps (i.e., amplification and hybridization) are preferably repeated at least once. For use in detection, the number of cycling steps will depend, e.g., on the nature of the sample. If the sample is a complex mixture of nucleic acids, more cycling steps may be required to amplify the target sequence sufficient for detection. Generally, the cycling steps are repeated at least about 20 times, but may be repeated as many as 40, 60, or even 100 times.

Fluorescent Resonance Energy Transfer (FRET)

FRET technology (see, for example, U.S. Pat. Nos. 4,996, 143, 5,565,322, 5,849,489, and 6,162,603) is based on the fact that when a donor and a corresponding acceptor fluorescent moiety are positioned within a certain distance of each other, energy transfer takes place between the two fluorescent moieties that can be visualized or otherwise detected and/or quantitated. As used herein, two oligonucleotide probes, each containing a fluorescent moiety, can hybridize to an amplification product at particular positions determined by the complementarity of the oligonucleotide probes to the *Legionella* target nucleic acid sequence. Upon hybridization of the oligonucleotide probes to the amplification product at the appropriate positions, a FRET signal is generated.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety preferably should be at least 100 nm greater than the wavelength maximum of the excitation spectrum of the donor fluorescent moiety. Accordingly, efficient non-radiative energy transfer can be produced therebetween.

Fluorescent donor and acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-RED 640 (LightCycler™-Red 640-N-hydroxysuccinimide ester), LC™-RED 705 (LightCycler™-Red 705-Phosphoramidite), cyanine dyes such as CY5 and CY5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm also is important, as the linker arms will affect the distance between the donor fluorescent moiety and the acceptor fluorescent moiety. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to particular nucleotide bases, and also for attaching fluorescent moieties to a linker arm.

An acceptor fluorescent moiety such as LC™-RED 640 (LightCycler™-Red 640-N-hydroxysuccinimide ester) can be combined with C6-Phosphoramidites (available from ABI (Foster City, Calif.) or Glen Research (Sterling, Va.)) to produce, for example, LC™-RED 640 (LightCycler™-Red 640-Phosphoramidite). Frequently used linkers to couple a donor fluorescent moiety such as fluorescein to an oligonucleotide include thiourea linkers (FITC-derived, for example, fluorescein-CPG's from Glen Research or ChemGene (Ashland. Mass)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of Legionella and L. pneumophila

The diagnosis of Legionella infection can be made from a number of specimen types, and by a number of testing modalities. Bacterial culture of bronchoscopy or lung biopsy specimens is the most sensitive means of detection to date. Specialized growth media such as Buffered Charcoal Yeast Extract (BCYE) is required for culture, with up to two weeks of incubation recommended to ensure maximal recovery. Isolates are typically identified using a combination of colony and gram stain morphology, with serologic confirmation and species identification obtained using specific fluorescein-labeled antibodies. Direct detection of organisms in uncultured clinical specimens, usually performed with immunofluorescent methods, is much more rapid than culture but the sensitivity of these methods is poor. A variety of means including radioimmunoassay, enzyme immunoassay, and latex agglutination can be used to detect a soluble polysaccharide antigen of L. pneumophila (serogroup 1 only) in urine with a reported sensitivity of 55–90%. Serological methods are highly sensitive, but their utility is generally limited to epidemiologic studies due to the time lag needed to detect seroconversion. A number of methods have been used in an attempt to identify Legionella organisms in paraffin-embedded tissue sections including various histochemical and immunohistochemical techniques. Silver impregnation stains (e.g., WS staining) serve as the current mainstay of detection in such tissues.

Assays based on molecular diagnostic techniques have included ISH using DNA probes, as well as PCR-based methods. Probes for ISH have largely been directed against rRNA sequences, with sensitivities of approximately 30–75% in both bronchoalveolar lavage (BAL) and fixed tissue specimens. PCR methodology has been used primarily against the 5S and 16S rRNA genes, and against mip of L. pneumophila. The latter amplification assays have been utilized for detection of Legionella species in environmental specimens, serum, urine, throat swabs and BAL specimens resulting in varying degrees of specificity.

Conventional molecular methods used in the above-noted studies require PCR-based amplification followed by detection using probe hybridization, usually on a solid substrate. These methods are labor intensive and frequently require at least one day to perform. Additionally, the required manipulation of post-amplification products increases the risk of carry-over contamination and false-positives. By using commercially available, rapid cycle, real-time PCR instrumentation (e.g., LIGHTCYCLER™, Roche Molecular Biochemicals, Indianapolis, Ind.). PCR amplification and detection can be combined in a single closed cuvette with dramatically reduced cycling time. This method obviates the need for further manipulation of the specimen, greatly reduces turn-around time, and diminishes the risk of cross-contamination between samples. Real-time PCR is an attractive alternative to conventional PCR techniques in the clinical laboratory.

The present invention provides methods for detecting the presence or absence of Legionella in a biological sample from an individual. Methods provided by the invention avoid problems of sample contamination, false-negatives, false-positives, and further allows the specific detection of L. pneumophila. The methods include performing at least one cycling step that includes amplifying and hybridizing. An amplification step includes contacting the sample with a pair of 5S rRNA primers to produce a 5S rRNA amplification product if Legionella 5S rRNA nucleic acid in present in the sample. Each of the 5S rRNA primers anneals to a target within or adjacent to a Legionella 5S rRNA nucleic acid molecule such that at least a portion of the amplification product contains nucleic acid sequence corresponding to 5S rRNA and, more importantly, such that the amplification product contains the nucleic acid sequences that are complementary to 5S rRNA probes. A hybridizing step includes contacting the sample with a pair of 5S rRNA probes. Generally, the members of the pair of 5S rRNA probes hybridize to the amplification product within no more than five nucleotides of each other. According to the invention, a first 5S rRNA probe of a pair of 5S rRNA probes can be labeled with a donor fluorescent moiety and a second 5S rRNA probe of a pair of 5S rRNA probes can be labeled with a corresponding acceptor fluorescent moiety. The method further includes detecting the presence or absence of FRET between the donor fluorescent moiety of the first 5S rRNA probe and the corresponding acceptor fluorescent moiety of the second 5S rRNA probe. Multiple cycling steps can be performed, preferably in a thermocycler. The above-described methods for detecting Legionella in a biological sample using primers and probes directed toward 5S rRNA also can be performed using other Legionella gene-specific primers and probes. In addition, the above-described methods for detecting Legionella in a biological sample using primers and probes directed toward the 5S rRNA also can be performed using mip-specific primers and mip-specific probes to specifically detect L. pneumophila infections.

As used herein, "amplifying" refers to the process of synthesizing nucleic acid molecules that are complementary to one or both strands of a template nucleic acid (e.g., Legionella nucleic acid molecules encoding 5S rRNA). Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing, and elongating steps each can be performed once. Generally, however, the denaturing, annealing, and elongating steps are performed multiple times such that the amount of amplification product is increasing, oftentimes exponentially, although exponential amplification is not required by the present methods. Amplification typically requires the presence of deoxyribonucleoside triphosphates, a DNA polymerase enzyme (e.g. PLATINUM® TAQ (derived from recombinant Taq DNA polymerase by binding of a thermolabile inhibitor containing monoclonal antibodies to Taq DNA polymerase such that the inhibitor is denatured during the initial denaturation step of PCR and active Taq DNA polymerase is released into the reaction)) and an appropriate buffer and/or co-factors for optimal activity of the polymerase enzyme (e.g. $MgCl_2$ and/or KCl)

If amplification of *Legionella* nucleic acid occurs and an amplification product is produced, the step of hybridizing results in a detectable signal based on FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of nucleic acid from *Legionella* or *L. pneumophila* in the biological sample and the absence of FRET indicates the absence of *Legionella* or *L. pneumophila* nucleic acids in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, a sample having three times the amount of FRET than that in a control sample lacking *Legionella* or *L. pneumophila* nucleic acid generally indicates a *Legionella* or *L. pneumophila* infection in the individual.

Representative biological samples that can be used in practicing the methods of the invention include sputum, bronchio-alveolar lavage, bronchial aspirates, lung tissue, urine or blood. Biological sample collection and storage methods are known to those of skill in the art. Biological samples can be processed (e.g., by standard nucleic acid extraction methods and/or using commercial kits) to release *Legionella* or *L. pneumophila* nucleic acid or, in some cases, the biological sample is contacted directly with the PCR reaction components and the appropriate oligonucleotides.

Melting curve analysis is an additional step that can be included in a cycling profile. Melting curve analysis is based on the fact that double-stranded nucleic acid "melts" into single strands at a characteristic temperature called the melting temperature (Tm), which is defined as the temperature at which half of the DNA duplexes have melted. The melting temperature of a nucleic acid depends primarily upon its nucleotide composition. Thus, nucleic acid molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the 5S rRNA probes or the mip probes from the respective amplification product can confirm the presence or absence of *Legionella* or *L. pneumophila*, respectively, in the sample.

Within each thermocycler run, control samples are cycled as well. Positive control samples can amplify control nucleic acid template (e.g., template other than the 5S rRNA or mip) using, for example, control primers and control probes. Positive control samples can also amplify, for example, a plasmid construct containing *Legionella* 5S rRNA or *L. pneumophila* mip nucleic acid. Such a plasmid control can be amplified internally (e.g., within each biological sample) or in separate samples run side-by-side with the patients' samples. Each thermocycler run should also include a negative control that, for example, lacks *Legionella* template DNA. Such controls are indicators of the success or failure of the amplification, hybridization, and/or FRET reaction.

Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are desirable for accuracy in a diagnostic laboratory handling clinical samples.

Conventional PCR methods in conjunction with FRET technology can be used to practice the methods of the invention. In one embodiment, a LIGHTCYCLER™ instrument is used. A detailed description of the LIGHTCYCLER™ System and real-time and on-line monitoring of PCR can be found on Roche's website. The following patent applications describe real-time PCR as used in the LIGHTCYCLER™ technology: WO 97/46707, WO 97/46714 and WO 97/46712. The LIGHTCYCLER™ instrument is a rapid thermocycler combined with a microvolume fluorimeter utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LIGHTCYCLER™ thermal chamber. Addition of selected fluorescent dyes to the reaction components allows the PCR to be monitored in real-time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LIGHTCYCLER™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorimeter, as part of the LIGHTCYCLER™ apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LIGHTCYCLER™ instrument (Roche Molecular Biochemicals, Catalog No. 2 011 468) includes three band-pass filters (530 nm, 640 nm, and 710 nm), providing three-color detection and several fluorescence acquisition options. The present invention, however, is not limited by the configuration of a commercially available instrument. Data collection Options include once per cycling step monitoring, fully continuous single-sample acquisition for melting curve analysis, continuous sampling (in which sampling frequency is dependent on sample number) and/or stepwise measurement of all samples after defined temperature interval.

The LIGHTCYCLER™ can be operated using a PC workstation and can utilize a Windows NT operating system.

Signals from the samples are obtained as the machine positions the capillaries sequentially over the optical unit. The software can display the fluorescence signals in real-time immediately after each measurement. Fluorescent acquisition time is 10–100 msec. After each cycling step, a quantitative display of fluorescence vs. cycle number can be continually updated for all samples. The data generated can be stored for further analysis.

A common FRET technology format utilizes two hybridization probes. Each probe can be labeled with a different fluorescent moiety and the two probes are generally designed to hybridize in close proximity to each other in a target DNA molecule (e.g., an amplification product). By way of example, a donor fluorescent moiety such as fluorescein can be excited at 470 nm by the light source of the LiGHTCYCLER™ Instrument. During FRET, fluorescein transfers its energy to an acceptor fluorescent moiety such as LC™-RED 640 (LIGHTCYCLER™-Red 640-N-hydroxysuccinimide ester) or LCW™ RED 705 (LightCycler™-Red 705-Phosphoramidite). The acceptor fluorescent moiety then emits light of a longer wavelength (e.g., 640 nm or 705 nm, respectively), which is detected by the optical detection system of the LIGHTCYCLER™ instrument. Other donor and corresponding acceptor fluorescent moieties suitable for use in the invention are described above. Efficient FRET can only take place when the fluorescent moieties are in direct local proximity (for example, within 5 nucleotides of each other as discussed above) and when the emission spectrum of the donor fluorescent moiety overlaps with the absorption spectrum of the acceptor fluorescent moiety. The intensity of the emitted signal can be correlated with the number of original target nucleic acid molecules (e.g., the number of Legionella or L. pneumophila organisms).

Another FRET technology format utilizes TAQMAN® technology to detect the presence or absence of an amplification product, and hence, the presence or absence of Legionella. TAQMAN® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TAQMAN® technology, and is suitable for performing the methods described herein for detecting Legionella. Information on PCR amplification and detection using an ABI PRISM® 770 system can be found on Applied Biosystems' website.

Yet another FRET technology format utilizes molecular beacon technology to detect the presence or absence of an amplification product, and hence, the presence or absence of Legionella. Molecular beacon technology uses a hybridization probe labeled with a donor fluorescent moiety and an acceptor fluorescent moiety. The acceptor fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., the amplification products), the secondary structure of the probe is disrupted and the fluorescent moieties become separated from one another such that after excitation with light of a suitable wavelength, the emission of the first fluorescent moiety can be detected.

As an alternative to detection using FRET technology, an amplification product can be detected using a nucleic acid binding dye such as a fluorescent DNA binding dye (e.g., SYBROREENI® or SYBRGOLD® (Molecular Probes)). Upon interaction with the double-stranded nucleic acid, such nucleic acid binding dyes emit a fluorescence signal after excitation with light at a suitable wavelength. A nucleic acid binding dye such as a nucleic acid intercalating dye also can be used. When nucleic acid binding dyes are used, a melting curve analysis is usually performed for confirmation of the presence of the amplification product.

It is understood that the present invention is not limited by the configuration of one or more commercially available instruments.

Articles of Manufacture

The invention further provides for articles of manufacture to detect Legionella and specifically L. pneumophila. An article of manufacture according to the present invention can include primers and probes used to detect Legionella, together with sutiable packaging material. Representative primers and probes provided in a kit for detection of Legionella can be complementary to Legionella nucleic acid molecules encoding 5S rRNA. Similarly, representative primers and probes for detection of L. pneumophila can be complementary to L. pneumophila nucleic acid molecules encoding mip. Methods of designing primers and probes are disclosed herein, and representative examples of primers and probes that amplify and hybridize to Legionella nucleic acids encoding 5S rRNA or mip are provided.

Articles of manufacture of the invention also can include one or more fluorescent moieties for labeling the probes or, alternatively, the probes supplied with the kit can be labeled. For example, an article of manufacture may include a donor fluorescent moiety for labeling one of the 5S rRNA or mip probes and a corresponding acceptor fluorescent moiety for labeling the other 5S rRNA or mip probe. Examples of suitable FRET donor fluorescent moieties and acceptor fluorescent moieties are provided herein.

Articles of manufacture of the invention also can contain a package insert having instructions thereon for using pairs of 5S rRNA primers and 5S rRNA probes to detect Legionella in a biological sample. Such a package insert may contain instructions thereon for using pairs of mip primers and mip probes to specifically detect L. pneumophila in a biological sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Control Organisms

All experiments to optimize PCR conditions, as well as dilution studies to evaluate sensitivity, and plasmid construction, were performed using L. pneumophila serogroup 1 (American Type Culture Collection (ATCC), Manassas, Va., Catalog No. 33152). Other strains of

*Legionella* used for validation of the assay are listed in Table 1 and included *L. pneumophila* serogroups 1–6, as well as several other non-pneumophilic strains of *Legionella*. Specificity of the assay was assessed using a panel of control strains of bacteria (Table 2) representing commonly isolated non-*Legionella* respiratory pathogens as well as non-pathogens that might be detected in respiratory specimens.

TABLE 1

Control Strains of *Legionella*

| Bacterial Strain | Source* | 5S rRNA PCR | mip PCR |
|---|---|---|---|
| *L. pneumophila* serogroup 1 | ATCC 33152 | + | + |
| *L. pneumophila* serogroup 1 | CDC Phil. strain | + | + |
| *L. pneumophila* serogroup 1 | | + | + |
| *L. pneumophila* serogroup 2 | | + | + |
| *L. pneumophila* serogroup 3 | | + | + |
| *L. pneumophila* serogroup 4 | | + | + |
| *L. pneumophila* serogroup 5 | | + | + |
| *L. pneumophila* serogroup 6 | | + | + |
| *L. longbeachae* | | + | − |
| *L. longbeachae* serogroup 1 | | + | − |
| *L. longbeachae* serogroup 2 | | + | − |
| *L. dumoffii* | | + | − |
| *L. dumoffii* | | + | − |
| *L. bozemanii* | ATCC 33204 | + | − |
| *L. micdadei* | | + | − |
| *L. micdadei* | ATCC 33623 | + | − |
| *L. jordanis* | | + | − |

*If not otherwise specified, strains represent Mayo Clinic isolates

Table 2-Specificity panel for *Legionella* LIGHTCYCLER™ PCR assays

TABLE 2

Specificity panel for *Legionella* LIGHTCYCLER ™ PCR assays

| Bacterial Strain | Source* | 5S PCR | mip PCR |
|---|---|---|---|
| *Stenotrophomonas maltophilia* | CDC AB9-D19-80 | − | − |
| *Morganella morganii* | | − | − |
| *Bordetella bronchoseptica* | | − | − |
| *Bordetella pertussis* | ATCC VR1310 | − | − |
| *Bordetella parapertussis* | ATCC 27853 | − | − |
| *Chlamydia pneumoniae* | ATCC 25922 | − | − |
| *Pseudomonas aeruginosa* | | − | − |
| *Escherichia coil* | CDC B2-003-72 | − | − |
| *Kiebsiella pneumoniae* | | − | − |
| *Streptococcus pneumoniae* | | − | − |
| *Mycoplasma pneumoniae* | | − | − |
| *Mycobacterium tuberculosis* | | − | − |
| *Mycobacterium Avium Complex* | CDC ABD-D20-82 | − | − |
| *Streptococcus* spp. *viridans* group | | − | − |
| *Listeria monocytogenes* | | − | − |
| *Staphylococcus epidermidis* | CDC AB4-BID-84 | − | − |
| *Aeromonas hydrophila* | | − | − |
| *Pseudomonas fluorescens* | | − | − |
| *Moraxella catarrhalis* | | − | − |
| *Mycoplasma pneumoniae* | | − | − |
| *Pseudomonas cepacia* | | − | − |
| *Acinetobacter* sp. | ATCC 25923 | − | − |
| *Kiebsiella oxytoca* | | − | − |
| *Staphylococcus aureus* | CDC AB4-B08-84 | − | − |
| *Proteus mirabilis* | | − | − |
| *Streptococcus pyogenes* | ATCC 10211 | − | − |
| *Proteus vulgaris* | | − | − |
| *Haemophilus influenzae* | | − | − |
| *Bacteroides fragilis* | CDC AB2-C15-82 | − | − |
| *Citrobacter freundii* | | − | − |
| *Campylobacter jejuni* | | − | − |

*If not otherwise specified, strains represent Mayo Clinic isolates

Example 2

Clinical Specimens

A retrospective review of positive *Legionella* culture results at the Mayo Clinic from 1979–1999 revealed 9 BAL specimens for which frozen, archived material was available. For 7 of these specimens, frozen cell suspensions were available for analysis; for the remaining 2 specimens, only supernatant was available. In addition, cell suspensions from 10 BAL specimens that were culture-negative for *Legionella* were randomly selected from similarly frozen material. These cell suspensions were originally prepared from BAL's using a cytospin method. Only cell suspensions having >2x10$^6$ cells counted by microscopy on a 4 mm$^2$ grid were cultured for *Legionella* spp. and frozen. Cultures of BAL or lung biopsy specimens were performed at the time the specimens were collected and were not repeated on frozen specimens during the present study. In all cases, results for *Legionella* using DFA performed on fresh specimens prior to freezing were also available. Retrospective review from 1979–1999 also revealed 9 open lung biopsy cases that were culture-positive for *Legionella* species and for which a total of 16 formalin-fixed paraffin-embedded tissue blocks were available for evaluation. Eight open lung biopsy specimens from the same time period all showing non-specific histological findings of pneumonia/pneumonitis, and all culture-negative for *Legionella* species were also selected for evaluation. A single tissue block was used from each of these culture-negative cases.

Example 3

BAL Processing and Culture Methodology

Prior to culture, BAL specimens were centrifuged for 15 min at 3300 rpm. The top 7.5 ml of the resulting suspension was removed. The remaining cell concentrate was mixed and used for culture. Fresh tissue from open lung biopsy specimens was homogenized in Enriched Brain Heart Infusion Broth (Difco, Becton-Dickinson, Sparks, Md.) prior to plating. Culture for *Legionella* species was performed on Buffered Charcoal Yeast Extract agar (BCYEα) and BCYEα with polymyxin B, anisomycin and vancomycin (Becton Dickinson Microbiology Systems, Sparks, Md.), and incubated at 35° C. at room temperature for up to 14 days. Organisms from characteristic colonies were Gram-stained and identified to the species level using a commercially available panel of fluorescein isothiacyanate (FITC)-labeled antibodies (SciMedx, Denville, N.J.).

Example 4

Histopathologic Examination

Hematoxylin and Eosin (H&E)-tissue sections and tissue sections for WS-staining were cut and stained, and consecutive sections of tissue were taken concurrently for ISH, DFA and PCR. All tissue sections were cut at 4 μm. H&E and WS stains were carried out using standard histologic laboratory methods. The WS stained slides were evaluated in a blinded manner. Positive cases for *Legionella*-like organisms showed dark brown-staining bacillary structures.

Example 5

Direct Fluorescent Antibody (DFA) Detection

Prior to direct examination, a fresh BAL specimen was centrifuged for 5 min at 2500 rpm and the resultant supernatant removed. In some cases, this supernatant was later used in the PCR assay (see 'Real Time PCR' below). The cell pellet was resuspended in normal saline with a lysis agent and/or mucolytic agents added as necessary. This cell suspension was used both for DFA and PCR (see 'Real Time PCR' below). For each smear to be examined by DFA, 200 µl was cytocentrifuged at 700 rpm for 7 min onto a clean glass slide and allowed to air-dry. Histologic sections were deparaffinized through xylene and graded ethanol dilutions and allowed to air-dry. DFA was performed per the manufacturer's instructions (SciMedX). Two polyvalent FITC-labeled rabbit anti-*Legionella* conjugate pools were applied to a separate replicate smear or tissue section. FITC-labeled negative rabbit globulin was applied to a third replicate of the specimen to serve as a negative control. Antibody pools were also applied to a positive control slide prepared from a known positive lung tissue in formalin. Positives were interpreted based on the presence of fluorescent bacillary structures in a given smear or section.

Example 6

In situ Hybridization (ISH)

In situ hybridization was performed by a procedure as previously described with some modifications:

Oligonucleotide Probes:

Two oligonucleotide probes (Table 3), both directed against the 16S rRNA sequence of *L. pneumophila* were used. One probe was previously described (Grimm et al., 1998, *Appl. Environ. Microbiol.,* 64:2686–90) and the other probe was designed based on the analysis of sequence matches and mismatches (using a GenBank BLAST search with *Legionella* 16S rRNA sequences). The specificity of probes was checked against the sequences of other bacteria, fungi, parasites, and animals using Genetic Computer Group (GCG) software (Madison, Wis.). Probes were 3'-tailed with digoxigenin-11-dUTP (Enzo Diagnostic, Inc), then diluted to a final concentration of 2.0 ng/µl in hybridization buffer.

Pretreatment of Sections for ISH:

After deparaffinizing and rehydration, paraffin sections were rinsed twice in diethyl pyrocarbonate (DEPC)-treated $H_2O$ for 2 min each. Endogenous alkaline phosphatase activity was quenched with 0.2 M HCl for 20 min at room temperature and slides were microwaved for 10 min in 10 mM citric acid (pH 6.0) and cooled to room temperature. Sections were then digested with 25 µg/ml proteinase K in 10 mM phosphate buffered saline (PBS) (pH 7.2) for 10 min at room temperature followed by acetylation for 15 min with freshly prepared 0.6% acetic anhydride in 0.1 M triethanolamine (pH 8.0). Pre-hybridization was performed for 30 min at room temperature using a mixture containing 50% deionized formamide, 10% dextran sulfate, 1× Denhardt's solution, 3× standard saline citrate (SSC), 100 µg/ml salmon sperm DNA, 125 µg/ml yeast tRNA, 10 µg/ml polyadenylic-cytidylic acid, 0.05 M Tris, 5 mM EDTA, 600 mM NaCl, and 0.1% sodium pyrophosphate-inorganic.

Hybridization and post-hybridization washes: Following pre-hybridization, residual prehybridization buffer was thoroughly removed from around the tissue section. An oligonucleotide probe cocktail specific for *L. pneumophila* (2 ng/µl in prehybridization buffer) was applied to sections. Slides were coverslipped with a SIGMACOTE® (silicone in heptane) (Sigma) coverglass, heat-treated at 95° C. for 5 min, and hybridized in a humid environment for three hrs at 50° C. Sections were rinsed twice in 2×SSC for 10 min at room temperature, washed in 0.5×SSC at 37° C. for 20 min, and rinsed twice in buffer A (1% normal sheep serum in 0.3% Triton X-100) for 2 min at room temperature.

Immunochemical Detection:

After post-hybridization washing, digoxigenin-labeled probes were detected according to the manufacturer's instructions (Digoxigenin Detection Kit; Boehringer Mannheim). Briefly, after pre-incubation of sections for 30 min in Blocking Buffer A (1% normal swine serum, 0.3% Triton X-100), the sections were incubated in a 1:200 dilution of alkaline phosphatase-conjugated anti-digoxigenin Fab fragment in Blocking Buffer A for 1 hr at room temperature. Rinsing with Buffer A and Buffer C (Tris-HCl and MgCl, pH 9.5) was performed, and sections were subsequently reacted with nitroblue-tetrazolium chloride (NBT) and 5-bromo-4-chloro-3-indolyphosphate (BCIP) forming an insoluble blue precipitate at the site of reaction. Sections were then rinsed in Buffer C, counterstained with 0.1% nuclear fast red, rinsed again in Buffer C, dehydrated in graded ethanols, cleared in xylene, and coverslipped with a xylene-based synthetic mounting medium. Positive interpretation of a slide was based on the presence of blue-staining bacillary structures against a pink-red background.

ISH Negative Controls and Probe Specificity Tests:

Negative controls used for ISH consisted of: 1) omission of the probes from the hybridization reaction; 2) slides hybridized with non-labeled probe; 3) cross reactivity testing for target specificity using an ISH probe for albumin hybridized to *Legionella*-positive tissue sections; and 4) cross reactivity testing for probe specificity using five additional cases with tissue involvement by other gram positive and gram negative bacteria.

Example 7

Real-Time PCR

PCR and, product detection were carried out simultaneously ("real-time PCR") using a LIGHTCYCLER™ instrument (Roche Molecular Biochemicals, Indianapolis, Ind.). The LIGHTCYCLER™ instrument is a combined thermocycler and fluorimeter that offers rapid PCR thermocycling (20–40 mm). Temperature is controlled with circulated heated and ambient air. Samples and PCR master mix are contained in 30 µl glass cuvettes. Sample detection is based on the principle of fluorescence resonance energy transfer (FRET) with adjacent hybridization probes directed against the intended PCR amplification product. With fluorescein serving as the donor fluorophore, and LC™RED 640 (LIGHTCYCLER™-Red 640-N-hydroxysuccinimide ester, Roche Molecular Biochemicals) serving as the acceptor fluorophore, the presence of a PCR amplification product can be assessed by detecting LC-RED 640 (LIGHTCYCLER™-Red 640-N-hydroxysuccinimide ester) fluorescence. Samples can be assayed for the presence of FRET signal during each PCR cycle, and the cycle number at which signal is first detected can be correlated to the original concentration of target. The specificity of amplification can be confirmed by melting curve analysis. A melting curve can be generated by depicting the negative derivative of fluorescence vs. temperature (-dF/dT) over the course of a gradual increase in temperature (see below, 'PCR Cycling and Melting Curve Conditions').

Extraction of Control Bacterial Strains:

Culture isolates used as control organisms were extracted by two different methods. In the case of Gram-negative isolates, including *Legionella* species, bacterial colonies were suspended in sterile H$_2$O to a turbidity of approximately 1 McFarland, lysed in a 100° C. heat block for 10 min and centrifuged for 1 min at 20,000× g. The resulting supernatant was used for analysis. In the case of Gram-positive isolates, bacterial colonies were suspended in 1.0 ml of 1 N NaOH to a turbidity of approximately 1 McFarland and incubated at room temperature for 5 min. The cells were pelleted, washed in an equal volume of 0.5 M Tris-HCl (pH 8.0), pelleted again, and resuspended in 100 µl H$_2$O. After heating in a 100° C. heat block for 10 min, the suspension was centrifuged for 1 min at 20,000× g, and the supernatant used for analysis. Control extracts were used at a final dilution of 1:100 in sterile H$_2$O. The presence of amplifiable DNA in specificity controls was verified by utilizing broad range 16S rDNA amplification by standard methods. A specific PCR assay for the major outer membrane protein was used to verify the presence of Chlamydia nucleic acid in a biological sample.

Extraction of BAL Specimens: BAL specimens were extracted using CHELEX 100 INSTAGENE™ MATRIX (Bio-Rad Laboratories, Hercules, Calif.). Briefly, the specimen was mixed thoroughly and 20 µl added to 200 µl of INSTAGENE™ MATRIX. The resulting solution was mixed and placed in a 100° C. heat block for 10 min. After mixing again, the sample was centrifuged for 2 min at 12,000 rpm. The resulting supernatant was used for analysis.

Extraction of Tissue Specimens: 25 µm thick tissue sections were cut consecutively with other sections that were used for DFA and ISH assays. The sections were each cut with a clean blade, and placed in a sterile glass tube. Sections were deparaffinized in xylene, washed twice in absolute ethanol, subjected to proteinase K digestion overnight at 55° C., and then placed in a 100° C. heat block for 15 min. Extractions were carried out using QIAAMP® DNA spin columns (Qiagen Inc., Valencia, Calif.), as per the manufacturer's protocol. DNA was eluted from the spin columns twice using 50 λl of elution buffer AE (QIAAMP® DNA Mini Kit) for each elution. Elution buffer was incubated in the column for 1 min at room temperature prior to the first elution, and for 5 min at room temperature prior to the second elution. The first and second eluants were analyzed separately by PCR.

Primers and Probes: The sequences of the primers and probes used herein are shown in Table 3. Amplicons were kept to a minimum length (105 bp for the 5S rRNA gene and 124 bp for the mip gene) in order to enhance the utility of these assays in formalin-fixed tissue. Probes were constructed in order to juxtapose donor (fluorescein) and acceptor (LC-RED 640 (LightCycler™-Red 640-N-hydroxysuccinimide ester)) fluorophore dyes when probes were annealed to an amplification product. The mip primer/probe set was constructed for species-specific detection of L. pneumophila. The 5S rRNA primer/probe set was constructed to allow detection of all common Legionella species. Due to constraints imposed by the size and sequence of the 5S rRNA amplicon, only a single probe was used for FRET detection of the 5S rRNA amplicon. The probe was labeled at its 5' end with LC-RED 640 (LightCycler™-Red 640-N-hydroxysuccinimide ester), while the fluoroscein label was placed near the 3' end of the reverse primer.

TABLE 3

Nucleic Acid Sequences and Labeling of Primers and Probes

| Assay/ purpose | Target | Product size | Name | Sequences/labels (5' → 3')[d] |
|---|---|---|---|---|
| ISH/Probe | L. pneumophila 16S M36026[a] | | P1[a] | ATC TGA CCG TCC CAG GTT (SEQ ID NO:8) |
| ISH/Probe | L. pneumophila 16S M36026[b] | | P2 | AGC TTT CAT CCA AAG ATA (SEQ ID NO:9) |
| PCR/ Primer | Legionella species 5S X05081[b] | 105 | L5F[c] | ACT ATA GCG ATT TGG AAC C (SEQ ID NO:1) |
| PCR/ Primer &Probe | Legionella species 5S X05081[b] | | L5RB[c] | GGC GAT GAC CTA CT[F]T TC (SEQ ID NO:2) |
| PCR/ Probe | Legionella species 5S X05081[b] | | L5P[c] | [R]CAT GAG GAA GCC TCA CAC TAT CA[P] (SEQ ID NO:3) |
| PCR/ Primer | L. pneumophila mip S72442[b] | 124 | LPmipAf | ACC GAA CAG CAA ATG AAA GA (SEQ ID NO:4) |
| PCR/ Primer | L. pneumophila mip S72442[b] | | LPmipAr | AAC GCC TGG CTT GTT TTT GT (SEQ ID NO:5) |
| PCR/ Probe | L. pneumophila mip S72442[b] | | LPP1 | AAC AAG TTT CAG AAA GAT TTG ATG GCA AAG[F] (SEQ ID NO:6) |
| PCR/ Probe | L. pneumophila mip S72442[b] | | LPP2 | [R]GTA CTG CTG AAT TCA ATA AGT AAG CGG ATG[P] (SEQ ID NO:7) |

[a]Previously described, as LEGPNE1, by Grimm et al., 1998, Appl Environ Microbiol, 64:2686–90.
[b]GeneBank accession number
[c]Modified from sequences described by Mahbubani et al., 1990, Mol. Cell. Probes, 4:175–87
[d]R refers to LightCycler ™ (LC) Red 640 fluorescent dye; F refers to LC fluorescein dye; P refers to phosphate 5S rRNA PCR Master Mix: A 5 µl aliquot of sample (5 µl of H$_2$O was used as a negative control for each run) was added to 15 µl of PCR mix in each sample cuvette. The PCR Master Mix consisted of: 50 mM KCl, 20 mM Tris-HCl (pH 8.4), 0.1 mM of each of the deoxyribonucleoside triphosphates, 6 mM MgCl$_2$, 0.5 µM of both 5S rRNA primers, 0.1 µM of the single 5S rRNA probe, 0.05% IGEPAL CA-630 (Sigma), 0.025% bovine serum albumin, and 0.025 U/µl of PLATINUM® TAQ DNA Polymerase (Life Technologies, Rockville, Md.) (derived from recombinant Taq DNA polymerase by binding of a thermolabile inhibitor containing monoclonal antibodies to Taq DNA polymerase such that the inhibitor is denatured during the initial denaturation step of PCR and active Taq DNA polymerase is released into the reaction).

mip PCR Master Mix: A 5 μl aliquot of sample (5 μl of H$_2$O was used as a negative control for each run) was added to 15 μl of PCR mix in each sample cuvette. The Master Mix consisted of: 50 mM KCl, 20 mM Tris-HCl (pH 8.4), 0.2 mM of each of the deoxyribonucleoside triphosphates, 6 mM MgCl$_2$, 0.5 μM of each mip primers, 0.2 μM of the fluorescein mip probe, 0.4 μM of the LC™-RED 640 (LightCycler™-Red 640-N-hydroxysuccinimide ester) mip probe, 0.05% IGEPAL CA-630 (Sigma), 0.025% bovine serum albumin, and 0.025 U/μl of PLATINUM® TAQ DNA Polymerase (Life Technologies).

PCR Cycling and Melting Curve Conditions: PCR reagents and specimen extracts were sealed in glass capillary cuvettes with plastic plugs, centrifuged to allow mixing and to drive the mix into the distal end of each tube, and then placed in the LIGHTCYCLER™ instrument. The cycling protocol was identical for both the mip and the 5S rRNA amplification reactions: 95° C. for 2 min, followed by 50 cycles of: denaturation at 95° C., immediately reduced to 57°C. for 10 sec for annealing, and extension for 5 sec at 72° C. Melting curves were generated by incubating the samples at 55° C. and slowly raising the temperature of the thermocycler to 85° C., during which time fluorescence was measured at frequent intervals (of about 3 sec or less). Analysis of PCR amplification and melting curves was carried out using LIGHTCYCLER™software.

Sensitivity and Inhibition Studies:

Sensitivity of both PCR assays was assessed by testing serial dilutions of a known number of colony forming units (CFU's) of L. pneumophila. PCR inhibition was assessed by spiking all culture and PCR-negative eluants from BAL and tissue specimens with low concentrations of L. pneumophila. The concentration of each organism used was within one log unit of each assay's limit of sensitivity. Inhibition was demonstrated by loss of amplification signal and/or by appearance of signal at a later cycle number than that seen with similar concentrations of organisms diluted in sterile water.

Example 8

Analysis of Results

For direct assays (WS, DFA, and ISH), positives were defined as the presence of 5 or more identifiable bacilli, with the proper staining characteristics as described above for the given assay. For the PCR assay, positives were defined as the presence of a fluorescent signal (either during PCR amplification, or during melting curve analysis) of at least 3 times the baseline level of fluorescence. Baseline fluorescence is defined as the signal from the negative control in each run. The results from culture assays were considered as the "gold standard" against which all other assays were compared. Several tissue isolates were originally designated as "Legionnaire's Disease *Bacillus*" (LDB) as they were recovered before methods were in use for species determination. These were all retrospectively classified as *L. pneumophila*, based on the results of ISH prior to experiments described herein. Analysis of results was based on the number of specimens, rather than on the number of cases or patients tested. For BAL's, cells and supernatants from a single lavage procedure were classified as a single specimen. A breakdown of results by case, as well as by specimen, is given in Tables 4 and 5.

TABLE 4

Comparison of Results for Bronchial Alveolar Lavage (BAL) Specimens

| Case # | Sample type | Culture Results | DFA | 5S rDNA PCR | mip PCR |
|---|---|---|---|---|---|
| 1 | Cells | L. pneumophila Group 3 | − | + | + |
| 2 | Cells | L. pneumophila Group 1 | − | + | + |
| 3 | Cells | L. pneumophila Group 1 | − | + | + |
| 4 | Cells | L. bozemanii | − | + | − |
| 5 | Supernatant | L. pneumophila Group 1 | + | + | + |
| 6 | Supernatant | L. micdadei | + | + | − |
| 7 | Supernatant and Cells | L. pneumophila Group 1 | − | −/+[a] | −/+[a] |
| 8 | Supernatant and Cells | L. pneumophila Group 1 | + | +/+[a] | +/+[a] |
| 9 | Cells | L. pneumophila Group 1 | − | + | + |
| 10 | Cells | − | − | − | − |
| 11 | Cells | − | − | − | − |
| 12 | Cells | − | − | − | − |
| 13 | Cells | − | − | − | − |
| 14 | Cells | − | − | − | − |
| 15 | Cells | − | − | − | − |
| 16 | Cells | − | − | − | − |
| 17 | Cells | − | − | − | − |
| 18 | Cells | − | − | − | − |
| 19 | Cells | − | − | − | − |
| | Total specimens | 9/19 | | 3/19 | 9/19 |
| | Total cases L. pneumophila | 7/19 | | | 7/19 |

[a]Supernatant Result/Cell Concentrate Result

TABLE 5

Comparison of Results for Open Lung Biopsies

| Case # | Slide | Culture[b] | 5S rDNA PCR 1st Eluant | 5S rDNA PCR 2nd Eluant | mip[a] PCR 1st Eluant | mip[a] PCR 2nd Eluant | WS | DFA | ISH[a] |
|---|---|---|---|---|---|---|---|---|---|
| 1 | O | Lp 1 | + | − | − | − | − | − | + |
| 1 | G | Lp 1 | − | − | − | − | + | − | + |
| 2 | E | Lp 1 | − | − | − | − | − | − | + |
| 2 | H | Lp 1 | − | + | − | − | + | − | + |
| 3 | B | Lboz | − | + | −[c] | −[c] | − | + | −[c] |
| 3 | N | Lboz | − | + | −[c] | −[c] | + | − | −[c] |
| 4 | M | LDB | − | − | − | − | − | + | + |
| 5 | P | LDB | − | − | − | − | − | − | + |

TABLE 5-continued

Comparison of Results for Open Lung Biopsies

| | | | 5S rDNA PCR | | mip[a] PCR | | | | |
|---|---|---|---|---|---|---|---|---|---|
| Case # | Slide | Culture[b] | 1st Eluant | 2nd Eluant | 1st Eluant | 2nd Eluant | WS | DFA | ISH[a] |
| 5 | C | LDB | − | − | − | − | − | − | + |
| 6 | D | LDB | + | + | + | − | + | + | + |
| 6 | L | LDB | − | + | − | + | + | + | + |
| 7 | I | LDB | + | + | − | − | + | + | + |
| 7 | K | LDB | + | + | − | − | + | + | + |
| 8 | A | Lp 1 | + | + | − | − | + | + | + |
| 9 | F | Lp 1 | + | − | − | − | + | − | + |
| 9 | J | LDB | − | + | − | − | + | − | + |
| Totals: | 16 Slides | 9 Cases | 6/16 | 9/16 11/16 | 1/14 | 1/14 2/14 | 10/16 | 7/16 | 14/14 |
| 10 | Q | neg | − | − | − | − | − | − | − |
| 11 | R | neg | − | − | − | − | − | − | − |
| 12 | S | neg | − | − | − | − | − | − | − |
| 13 | T | neg | − | − | − | − | − | − | − |
| 14 | U | neg | − | − | − | − | − | − | − |
| 15 | V | neg | − | − | − | − | − | − | − |
| 16 | W | neg | − | − | − | − | − | − | − |
| 17 | X | neg | − | − | − | − | − | − | − |
| Totals: | 8 | 8 | 8 | 8 | 8 | 8 | 8 | 8 | 8 |

[a]mip PCR and ISH assays were both directed only at *L. pneumophila*; non-pneumophila cases were not included in evaluation of these tests.
[b]Lp 1: *L. pneumophila*, Group 1; LDB: Legionnaire's Disease Bacillus (when these tissue specimens were collected, they were not identified to the species level because FA conjugates for species identification of isolated colonies were not available. LDB organisms were identified as *L. pneumophila* from the ISH assay performed in the current study. As these specimens were fixed in formalin, it was not possible to culture them at the time the current study was performed).
Lboz: *L. bozemanii*
[c]Results negative, but this assay was not designed for detection of *Legionella bozemanii*.

Example 9

Validation of PCR Assay on Culture Isolates

*Legionella* primer and probe sets were tested against a total of 17 different known strains of *Legionella* (Table 1). All *Legionella* species and strains were detected by the *Legionella* 5S rDNA primers and probe, and all *L. pneumophila* serotypes were detected by the mip primers and probes. Both PCR assays showed 100% specificity (Table 2), with no evidence of cross-reactivity against any of the non-*Legionella* isolates. Both the *Legionella* and the *L. pneumophila* assay showed sensitivity down to <10 CFU level when used with serial dilutions of a know concentration of control organism.

Example 10

Bronchoalveolar Lavage (BAL) Specimens

As shown in Tables 4 and 6, the 5S rRNA *Legionella* assay detected 9/9 culture-positive specimens (100% clinical sensitivity), including 2 non-*L. pneumophila* species (*L. bozemanii* and *L. micdadei*). All 10 culture-negative specimens were negative by the LC-PCR assay (10/10, 100% specificity). Similarly, the mip *L. pneumophila* assay detected 7/7 *L. pneumophila* culture-positive specimens and 12/12 specimens were correctly assigned a negative score for *L. pneumophila* (100% sensitivity and 100% specificity). Inhibition studies showed minimal evidence of inhibitory effect for each of the 10 *Legionella*-negative extracts, based on the ability to detect low concentrations of spiked organisms. Results of inhibition assays were similar for both the 5S rRNA *Legionella* and the mip *L. pneumophila* assays. Only 3/9 *Legionella* culture-positive specimens were detected by DFA (33% sensitivity and 100% specificity).

TABLE 6

Sensitivities and Specificities of All Assays Evaluated*

| Assay evaluated/ results | Number of specimens culture-positive | Number of specimens culture-negative | Sensitivity (%) | Specificity (%) |
|---|---|---|---|---|
| BAL Samples | | | | |
| *Legionella* | | | | |
| LC-PCR[a] | | | | |
| Positive | 9 | 0 | 100 | 100 |
| Negative | 0 | 10 | | |
| DFA (genus pool) | | | | |
| Positive | 3 | 0 | 33 | 100 |
| Negative | 6 | 10 | | |
| *L. pneumophila* | | | | |
| LC-PCR[b] | | | | |
| Positive | 7 | 0 | 100 | 100 |
| Negative | 0 | 12 | | |
| Open Lung Biopsy Samples | | | | |
| *Legionella* | | | | |
| LC-PCR[a] | | | | |
| Positive | 11 | 0 | 69 | 100 |
| Negative | 5 | 8 | | |
| DFA (genus pool) | | | | |
| Positive | 7 | 0 | 44 | 100 |
| Negative | 9 | 8 | | |
| WS | | | | |
| Positive | 10 | 0 | 63 | 100 |
| Negative | 6 | 8 | | |

TABLE 6-continued

Sensitivities and Specificities of All Assays Evaluated*

| Assay evaluated/ results | Number of specimens culture-positive | Number of specimens culture-negative | Sensitivity (%) | Specificity (%) |
|---|---|---|---|---|
| L. pneumophila LC-PCR[b] | | | | |
| Positive | 2 | 0 | 17 | 100 |
| Negative | 12 | 8 | | |
| L. pneumophila ISH[c] | | | | |
| Positive | 14 | 0 | 100 | 100 |
| Negative | 0 | 10 | | |

[a]Assay target is 5S rDNA and is genus specific only.
[b]Assay target is mip gene and is L. pneumophila species-specific.
[c]Assay target is 16S rDNA and is L. pneumophila species-specific.

Example 11

Open Lung Biopsy Specimens

Tables 5 and 6 show the results obtained from open lung biopsy specimens. The method used most commonly by surgical pathologists, examination of WS stained slides, showed positive results in 10/16 specimens that were culture-positive for Legionella species (63% sensitivity). There were no false-positives when using WS staining (100% specificity). The sensitivity and specificity for the DFA method was 44% (7/16 culture-positive specimens detected) and 100%, respectively. ISH detected all 14 L. pneumophila culture-positive specimens (100% sensitivity and 100% specificity). As noted previously, the ISH assay was not designed for detection of non-L. pneumophila species, therefore the slides with L. bozemanii were counted as culture-negative for the purposes of this analysis. Specificity controls, including specimens which were culture-negative for Legionella, probe-negative assays, assays performed with non-labeled probe, as well as both target and probe cross reactivity assays, were all negative.

PCR was performed separately on the first and second 50 μl eluants obtained from extracting the open lung biopsy specimen. Table 4 shows the results of these two eluants separately and combined for each specimen. In all, 11/16 tissue specimens tested positive for Legionella (69% sensitivity) using the Legionella 5S rRNA primer/probe set. Although not uniformly advantageous, the second eluant showed a higher rate of positivity (9 slides positive) than the first eluant (6 slides positive). The L. pneumophila assay using mip primers and probes was less sensitive, with positives in only 2/14 cases (17% sensitivity). Inhibition assays, performed with the extracts of culture-negative cases, showed similar results for both the Legionella spp. and the L. pneumophila species-specific assays. Minimal inhibition was observed with the second eluant from the open lung biopsy extracts. In contrast, the first eluant showed variable, but in some cases marked, inhibition.

Example 12

Turn-Around Time

Legionella culture, while usually positive in 3–5 days, is not reported as negative by Mayo Laboratories until a full 2-week incubation period has elapsed. DFA of BAL specimens, including BAL prep/cytospin, requires 1–2 hrs. Similarly, real-time PCR of BAL specimens requires approximately 1–2 hrs, including sample preparation, cycling and detection. Studies performed on fixed tissue sections require more time, due to the need for overnight tissue processing and paraffin embedding. Including that processing time, WS, DFA, and ISH on tissue all require about 24 hour for assay turn-around. Real-time PCR of tissue requires an additional overnight protease digestion, bringing its reporting time to 2 days.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said pair of 5S rRNA primers comprises a first 5S rRNA primer and as second 5S rRNA primer, wherein said first 5S rRNA primer comprises the sequence 5'-ACT ATA GCG ATT TGG AAC C-3' (SEQ ID NO:1), wherein said hybridizing step comprises contacting said sample with a pair of 5S rRNA probes, wherein the members of said pair of 5S rRNA probes hybridize to said amplification product within no more than five nucleotides of each other, wherein a first 5S rRNA probe of said pair of 5S rRNA probes is labeled with a donor fluorescent moiety and wherein a second 5S rRNA probe of said pair of 5S rRNA probes is labeled with a corresponding acceptor fluorescent moiety; and detecting the presence or absence of fluorescence resonance energy transfer (FRET) between said donor fluorescent moiety of said first 5S rRNA probe and said acceptor fluorescent moiety of said second 5S rRNA probe, wherein the presence of FRET is indicative of the presence of *Legionella* in said biological sample, and wherein the absence of FRET is indicative of the absence of *Legionella* an said biological sample.

2. The method of claim 1, wherein said second 5S rRNA primer comprises the sequence 5'-GGC GAT GAC CTA CTT TC-3' (SEQ ID NO:2).

3. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said pair of 5S rRNA primers comprises a first 5S rRNA primer and a second 5S rRNA primer, wherein said second 5S rRNA primer comprises the Sequence 5'-GGC GAT GAC CTA CTT TC-3' (SEQ ID NO:2), wherein said hybridizing step comprises contacting said sample with a pair of 5S rRNA probes, wherein the members of said pair of 5S rRNA probes hybridize to said amplification product within no more than five nucleotides of each other, wherein a first 5S rRNA probe of said pair of 5S rRNA probes is labeled with a donor fluorescent moiety and wherein a second 5S rRNA probe of said pair of 5S rRNA probes is labeled with a corresponding acceptor fluorescent moiety; and detecting the presence or absence of fluorescence resonance energy transfer (FRET) between said donor fluorescent moiety of said first 5S rRNA probe and said acceptor fluorescent moiety of said second 5S rRNA probe, wherein the presence of FRET is indicative of the presence of *Legionella* in said biological sample, and wherein the absence of FRET is indicative of the absence of *Legionella* in said biological sample.

4. The method of claim 3, wherein said first 5S rRNA primer comprises the sequence 5'-ACT ATA GCG ATT TGG AAC C-3' (SEQ ID NO:1).

5. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said hybridizing step comprises contacting said sample with a pair of 5S rRNA probes, wherein the members of said pair of 5S rRNA probes hybridizing to said amplification product within no more than five nucleotides of each other, wherein a first 5S rRNA probe of said pair of 5S rRNA probes is labeled with a donor fluorescent moiety and wherein a second 5S rRNA probe of said pair of 5S rRNA probes is labeled with a corresponding acceptor fluorescent moiety, wherein said first 5S rRNA probe comprises the sequence 5'-CAT GAG GAA GCC TCA CAC TAT CA-3' (SEQ ID NO:3); and detecting the presence or absence of fluorescence resonance energy transfer (FRET) between said donor fluorescent moiety of said first 5S rRNA probe and said acceptor fluorescent moiety of said second 5S rRNA probe, wherein the presence of FRET is indicative of the presence of *Legionella* in said biological sample, and wherein the presence of FRET is indicative of the absence of *Legionella* in said biological sample.

6. The method of claim 5, wherein said second 5S rRNA probe comprises the sequence 5'-GGC GAT GAC CTA CTT TC-3' (SEQ ID NO:2).

7. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said hybridizing step comprises contacting said sample with a pair of 5S rRNA probes, wherein the members of said pair of 5S rRNA probes hybridize to said amplification product within no more than five nucleotides of each other, wherein a first 5S rRNA probe of said pair of 5S rRNA probes is labeled with a donor fluorescent moiety and wherein a second 5S rRNA probe of said pair of 5S rRNA probes is labeled with a corresponding acceptor fluorescent moiety, wherein said second 5S rRNA probe comprises the sequence 5'-GGC GAT GAC CTA CTT TC-3' (SEQ ID NO:2); and detecting the presence or absence of fluorescence resonance energy transfer (FRET) between said donor fluorescent moiety of said first 5S rRNA probe and said acceptor fluorescent moiety of said second 5S rRNA probe, wherein the presence of FRET is indicative of the presence of *Legionella* in said biological sample, and wherein the absence of FRET is indicative of the absence of *Legionella* in said biological sample.

8. The method of claim 7, wherein said first 5S rRNA probe comprises the sequence 5'-CAT GAG GAA GCC TCA CAC TAT CA-3' (SEQ ID NO:3).

9. The method of claim 1, 3, 5, or 7 wherein the presence of said FRET in an amount at least 3 times the amount of FRET in a sample lacking said *Legionella* 5S rRNA nucleic acid molecule is indicative of the presence of a *Legionella* infection in said individual.

10. The method of claim 1, 3, 5, or 7 wherein said cycling step is performed on a control sample.

11. The method of claim 10 wherein said control sample comprises said portion of said *Legionella* nucleic acid molecule encoding said 5S rRNA.

12. The method of claim 1, 3, 5, or 7 wherein said cycling step uses a pair of control primers and a pair of control probes, wherein said control primers and said control probes are other than said 5S rRNA primers and said 5S rRNA probes, wherein a control amplification product is produced if control template is present in said sample, wherein said control probes hybridize to said control amplification product.

13. The method of claim 1, 3, 5, or 7 further comprising:
performing at least one cycling step, wherein said cycling step comprises an amplifying step and a hybridizing step, wherein said amplifying step comprises contacting said sample with a pair of mip primers to produce a mip amplification product if a *Legionella pneumophila* nucleic acid molecule encoding macrophage infectivity potentiator (mip) is present in said sample, wherein said hybridizing step comprises contacting said sample with a pair of mip probes, wherein the members of said pair of mip probes hybridize within no more than five nucleotides of each other, wherein a first nip probe of said pair of mip probes is labeled with a donor fluorescent moiety and wherein a second mip probe or said pair of mip probes is labeled with a corresponding acceptor fluorescent moiety; and detecting the presence or absence of FRET between said donor fluorescent moiety or said first mip probe and said acceptor fluorescent moiety of said second mip probe upon hybridization of said pair of mip probes to said targets.

14. The method of claim 13, wherein said pair of mip primers comprises a first mip primer and a second mip primer, wherein said first mip primer comprises the sequence 5'-ACC GAA CAG CAA ATG AAA GA-3' (SEQ ID NO:4), and wherein said second mip primer comprises the sequence 5'-AAC GCC TGG CTT GTT TTT GT-3' (SEQ ID NO:5).

15. The method of claim 13, wherein said first mip probe comprises the sequence 5'-AAC AAG TTT CAG AAA GAT TTG ATG GCA AAG-3' (SEQ ID NO:6), and wherein said second mip probe comprises the sequence 5'-GTA CTG CTG AAT TCA ATA AGT AAG CGG ATG-3' (SEQ ID NO:7).

16. A method for detecting the presence or absence of *L. pneumophila* in a biological sample from an individual, said method comprising:
performing at least one cycling step, wherein a cycling step comprises an amplifying step and a hybridizing step, wherein said amplifying step comprises contacting said sample with a pair of mip primers to produce a mip amplification product if a *L. pneumophila* nucleic acid molecule encoding mip is present in said sample, wherein said pair of mip primers comprises a first mip primer and a second mip primer, wherein said first mip primer comprises the sequence 5'-ACC GAA CAG CAA ATG AAA GA-3' (SEQ ID NO:4), wherein said hybridizing step comprises contacting said sample with a pair of mip probes, wherein the members of said pair of mip probes hybridize within no more than five nucleotides of each other, wherein a first mip probe of said pair of mip probes is labeled with a donor fluorescent moiety and wherein a second mip probe of said pair of mip probes is labeled with a corresponding acceptor fluorescent moiety; and detecting the presence or absence of fluorescence resonance energy transfer (FRET) between said donor fluorescent moiety of said first mip probe and said acceptor fluorescent moiety of said second mip probe upon hybridization of said pair of mip probes to said targets, wherein the presence of FRET is indicative of the presence of *L. pneumophila* in said biological sample, and wherein the absence of FRET is indicative of the absence of *L. pneumophila* in said biological sample.

17. The of method of claim 16, wherein said second mip primer comprises the sequence 5'-AAC GCC TGG CTT GTT TTT GT-3' (SEQ ID NO:5).

18. A method for detecting the presence or absence of *L. pneumophila* in a biological sample from an individual, said method comprising:
performing at least one cycling step, wherein a cycling step comprises an amplifying step and a hybridizing step, wherein said amplifying step comprises contacting said sample with a pair of mip primers to produce a mip amplification product if a *L. pneumophila* nucleic acid molecule encoding mip is present in said sample, wherein said pair of mip primers comprises a first mip primer and a second mip primer, wherein said second mip primer comprises the sequence 5'-AAC GCC TGG CTT GTT TTT GT-3' (SEQ ID NO:5), wherein said hybridizing step comprises contacting said sample with a pair of mip probes, wherein the members of said pair of mip probes hybridize within no more than five nucleotides of each other, wherein a first mip probe of said pair of mip probes is labeled with a donor fluorescent moiety and wherein a second probe of said pair of mip probes is labeled with a corresponding acceptor fluorescent moiety; and detecting the presence or absence of fluorescence resonance energy transfer (FRET) between said donor fluorescent moiety of said first mip probe and said acceptor fluorescent moiety of said second mip probe upon hybridization of said pair of mip probes to said targets, wherein the presence of FRET is indicative of the presence of *L. pneumophila* in said biological sample, and wherein the absence of FRET is indicative of the absence of *L. pneumophila* in said biological sample.

19. The method of claim 18, wherein said first mip primer comprises the sequence 5'-ACC GAA CAG CAA ATG AAA GA-3' (SEQ ID NO:4).

20. A method for detecting the presence or absence of *L. pneumophila* in a biological sample from an individual, said method comprising:

performing at least one cycling step, wherein a cycling step comprises an amplifying step and a hybridizing step, wherein said amplifying step comprises contacting said sample with a pair of mip primers to produce a mip amplification product if a *L. pneumophila* nucleic acid molecule encoding mip is present in said sample, wherein said hybridizing step comprises contacting said sample with a pair of mip probes, wherein the members of said pair of mip probes hybridize within no more than five nucleotides of each other, wherein a first mip probe of said pair of mip probes is labeled with a donor fluorescent moiety and wherein a second mip probe of said pair of mip probes is labeled with a corresponding acceptor fluorescent moiety, wherein said first mip probe comprises the sequence 5'-AAC AAG TTT CAG AAA GAT TTG ATG GCA AAG-3' (SEQ ID NO:6); and detecting the presence or absence of fluorescence resonance energy transfer (FRET) between said donor fluorescent moiety of staid first mip probe and said acceptor fluorescent moiety of said second mip probe upon hybridization of said pair of mip probes to said targets, wherein the presence of FRET is indicative of the presence of *L. pneumophila* in said biological sample, and wherein the absence of FRET is indicative of the absence of *L. pneumophila* in said biological sample.

21. The method of claim 20, wherein said second mip probe comprises the sequence 5'-GTA CTG CTG AAT TCA ATA AGT AAG CGG ATG-3' (SEQ ID NO:7).

22. A method for detecting the presence or absence of *L. pneumophila* in a biological sample from an individual, said method comprising:

performing at least one cycling step, wherein a cycling step comprises an amplifying step and a hybridizing step, wherein said amplifying step comprises contacting said sample with a pair of mip primers to produce a mip amplification product if a *L. pneumophila* nucleic acid molecule encoding mip is present in said sample, wherein said hybridizing step comprises contacting said sample with a pair of mip probes, wherein the members of said pair of mip probes hybridize within no more than five nucleotides of each other, wherein a first mip probe of said pair of mip probes is labeled with a donor fluorescent moiety and wherein a second mip probe of said pair of mip probes is labeled with a corresponding acceptor fluorescent moiety, wherein said second snip probe comprises the sequence 5'-GTA CTG CTG AAT TCA ATA ACT AAG CGG ATG-3' (SEQ ID NO:7); and detecting the presence or absence of fluorescence resonance energy transfer (FRET) between said donor fluorescent moiety of said first mip probe and said acceptor fluorescent moiety of said second snip probe upon hybridization of said pair of snip probes to said targets, wherein the presence of FRET is indicative of the presence of *L. pneumophila* in said biological sample, and wherein the absence of FRET is indicative of the absence of *L. pneumophila* in said biological sample.

23. The method of claim 22, wherein said first mip probe comprises the sequence 5'-AAC AAG TTT CAG AAA GAT TTG ATG GCA AAG-3' (SEQ ID NO:6.

24. The method of claim 16, 18, 20, or 22, wherein the presence of said FRET in an amount at least 3 times the amount of FRET in a sample lacking said *L. pneumophila* mip nucleic acid molecule is indicative of the presence of a *L. pneumophila* infection in said individual.

25. The method of claim 16, 18, 20, or 22, wherein said cycling step is performed on a control sample.

26. The method of claim 25, wherein said control sample comprises said portion of said *L. pneumophila* nucleic acid molecule encoding said mip.

27. The method of claim 16, 18, 20, or 22, wherein said cycling step uses a pair of control primers and a pair of control probes, wherein said control primers and said control probes are other than said snip primers and said mip probes, wherein a control amplification product is produced if control template is present in said sample, wherein said control probes hybridize to said control amplification product.

28. The method of claim 1, 3, 5, 7, 16, 18, 20, or 22, wherein the members of said pair of probes hybridize within no more than two nucleotides of each other.

29. The method of claim 1, 3, 5, 7, 16, 18, 20, or 22, wherein the members of said pair of probes hybridize within no more than one nucleotide of each other.

30. The method of clam 1, 3, 5, 7, 16, 18, 20, or 22, wherein said donor fluorescent moiety is fluorescein.

31. The method of claim 1, 3, 5, 7, 16, 18, 20, or 22, wherein said detecting step comprises exciting said biological sample at a wavelength absorbed by said donor fluorescent moiety and visualizing and/or measuring the wavelength emitted by said acceptor fluorescent moiety.

32. The method of claim 1, 3, 5, 7, 16, 18, 20, or 22, wherein said detecting comprises quantitating said FRET.

33. The method of claim 1, 3, 5, 7, 16, 18, 20, or 22, wherein said detecting step is performed after each cycling step.

34. The method of claim 1, 3, 5, 7, 16, 18, 20, or 22, wherein said detecting step is performed in real time.

35. The method of claim 1, 3, 5, 7, 16, 18, 20, or 22, further comprising determining the melting temperature between one or both of said probe(s) and said amplification product, wherein said melting temperature confirms said presence or said absence of said *Legionella* or *L. pneumophila*.

36. The method of claim 1, 3, 5, 7, 16, 18, 20, or 22, further comprising preventing amplification of a contaminant nucleic acid.

37. The method of claim 36, wherein said preventing comprises performing said amplifying step in the presence of uracil.

38. The method of claim 37, wherein said preventing further comprises treating said biological sample with uracil-DNA glycosylase prior to a first amplification step.

39. The method of claim 1, 3, 5, 7, 16, 18, 20, or 22, wherein said biological sample is selected from the group consisting of sputum, bronchio-alveolar lavage, bronchial aspirates, lung tissue, urine and blood.

40. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said pair of 5S rRNA primers comprises a first 5S rRNA primer and a second 5S rRNA primer, wherein said first 5S rRNA primer comprises the sequence 5'-ACT ATA GCG ATT TGG AAC C-3' (SEQ ID NO:1), wherein said hybridizing step comprises contacting said sample with a 5S rRNA probe, wherein said 5S rRNA probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said 5S rRNA probe, wherein the presence or absence of FRET is indicative of the presence or absence of *Legionella* in said sample.

41. The method of claim 40, wherein said second 5S rRNA primer comprises the sequence 5'-GGC GAT GAC CTA CTT TC-3' (SEQ ID NO:2).

42. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said pair of 5S rRNA primers comprises a first 5S rRNA primer and a second 5S rRNA primer, wherein said second 5S rRNA primer comprises the sequence 5'GGC GAT GAC CTA CTT TC-3' (SEQ ID NO:2), wherein said hybridizing step comprises contacting said sample with a 5S rRNA probe, wherein said 5S rRNA probe is labeled with a donor fluorescent moiety and a corresponding acceptor fluorescent moiety; and detecting the presence or absence of fluorescent resonance energy transfer (FRET) between said donor fluorescent moiety and said acceptor fluorescent moiety of said 5S rRNA probe, wherein the presence or absence of FRET is indicative of the presence or absence of *Legionella* in said sample.

43. The method of claim 42, wherein said first 5S rRNA primer comprises the sequence 5'-ACT ATA GCG ATT TGG AAC C-3' (SEQ ID NO:1).

44. A method for detecting the presence or absence of *Legionella* in a biological sample from an individual, said method comprising:

performing at least one cycling step, wherein a cycling step comprises an amplifying step and a hybridizing step, wherein said amplifying step comprises contacting said sample with a pair of 5S rRNA primers to produce a 5S rRNA amplification product if a *Legionella* 5S rRNA nucleic acid molecule is present in said sample, wherein said hybridizing step comprises contacting said sample with a 5S rRNA probe, wherein said 5S rRNA probe is labeled with a donor fluorescent moiety and a corresponding acceptor fluorescent moiety, wherein said 5S rRNA probe comprises a sequence selected from the group consisting of 5'-CAT GAG GAA GCC TCA CAC TAT CA-3' (SEQ ID NO:3) and 5'-GGC GAT GAC CTA CTT TC-3' (SEQ ID NO:2); and detecting the presence or absence of fluorescence resonance energy transfer (FRET) between said donor fluorescent moiety and said acceptor fluorescent moiety of said 5S rRNA probe, wherein the presence or absence of FRET is indicative of the presence or absence of *Legionella* in said sample.

45. The method of claim 44, wherein said first and second 5S rRNA primers comprise the sequences 5'-ACT ATA GCG ATT TGG AAC C-3' (SEQ ID NO:1) and 5'-GGC GAT GAC CTA CTT TC-3' (SEQ ID NO:2), respectively.

46. A method for detecting the presence or absence of *L. pneumophila* in a biological sample from an individual, said method comprising:

performing at least one cycling step, wherein a cycling step comprises an amplifying step and a hybridizing step, wherein said amplifying step comprises contacting said sample with a pair of mip primers to produce a mip amplification product if a *L. pneumophila* mip nucleic acid molecule is present in said sample, wherein said pair of mip primers comprises a first mip primer and a second mip primer, wherein said first mip primer comprises the sequence 5'-ACC GAA CAG CAA ATG AAA GA-3' (SEQ ID NO:4), wherein said hybridizing step comprises contacting said sample with a mip probe, wherein said mip probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said mip probe, wherein the presence or absence of FRET is indicative of the presence or absence of *Legionella* in said sample.

47. The method of claim 46, wherein said second mip primer comprises the sequence 5'-AAC GCC TGG CTT GTT TTT GT-3' (SEQ ID NO:5).

48. A method for detecting the presence or absence or *L. pneumophila* in a biological sample from an individual, said method comprising:

performing at least one cycling step, wherein a cycling step comprises an amplifying step and a hybridizing step, wherein said amplifying step comprises contacting said sample with a pair of mip primers to produce a mip amplification product if a *L. pneumophila* mip nucleic acid molecule is present in said sample, wherein said pair of mip primers comprises a first mip primer and a second mip primer, wherein said second mip primer comprises the sequence 5'-AAC GCC TGG CTT GTT TTT GT-3' (SEQ ID NO:5), wherein said hybridizing step comprises contacting said sample with a mip probe, wherein said mip probe is labeled with a donor fluorescent moiety and a corresponding acceptor fluorescent moiety, and detecting the presence or absence of fluorescence resonance energy transfer (FRET) between said donor fluorescent moiety and said acceptor fluorescent moiety of said mip probe, wherein the presence or absence of FRET is indicative of the presence or absence of *Legionella* in said sample.

49. The method of claim 48, wherein said first mip primer comprises the sequence 5'-ACC GAA CAG CAA ATG AAA GA-3' (SEQ ID NO:4).

50. A method for detecting the presence or absence of *L. pneumophila* in a biological sample from an individual, said method comprising:

performing at least one cycling step, wherein a cycling step comprises an amplifying step and a hybridizing step, wherein said amplifying step comprises contacting said sample with a pair of mip primers to produce a mip amplification product if a *L. pneumophila* mip nucleic acid molecule is present in said sample, wherein said hybridizing step comprises contacting said sample with a mip probe, wherein said mip probe is labeled with a donor fluorescent moiety and a corresponding acceptor fluorescent moiety, wherein said mip probe comprises a sequence selected from the group consisting of 5'-AAC AAG TTT CAG AAA GAT TTG ATG GCA AAG-3' (SEQ ID NO:6) and 5'-GTA CTG CTG AAT TCA ATA AGT AAG CGG ATG-3' (SEQ ID NO:7); and detecting the presence or absence of fluorescence resonance energy transfer (FRET) between said donor fluorescent moiety and said acceptor fluorescent moiety of said mip probe, wherein the presence or absence of FRET is indicative of the presence or absence of *Legionella* in said sample.

51. The method of claim 50, wherein said first and second mip primers comprise the sequences 5'-ACC GAA CAG CAA ATG AAA GA-3' (SEQ ID NO:4) and 5'-AAC GCC TGG CTT GTT TTT GT-3' (SEQ ID NO:5).

52. The method of claim 40, 42, 44, 46, 48, or 50, wherein said amplification employs a polymerase enzyme having 5' to 3' exonuclease activity.

53. The method of claim 40, 42, 44, 46, 48, or 50, wherein said donor and acceptor fluorescent moieties are within no more than 5 nucleotides of each other on said probe.

54. The method of claim 53, wherein said acceptor fluorescent moiety is a quencher.

55. The method of claim 40, 42, 44, 46, 48, or 50, wherein said probe comprises a nucleic acid sequence that permits secondary structure formation, wherein said secondary structure formation results in spatial proximity between said donor and said acceptor fluorescent moiety.

56. The method of claim 55, wherein said acceptor fluorescent moiety is a quencher.

57. A method for detecting the presence or absence of *Legionella* in a biological sample from an individual, said method comprising:

performing at least one cycling step, wherein a cycling step comprises an amplifying step and a dye-binding step, wherein said amplifying step comprises contacting said sample with a pair of 5S rRNA primers to produce a 5S rRNA amplification product if a *Legionella* 5S rRNA nucleic acid molecule is present in said sample, wherein said pair of 5S rRNA primers comprises a first 5S rRNA primer and a second 5S rRNA primer, wherein said first 5S rRNA primer comprises the sequence 5'-ACT ATA GCG ATT TGG AAC C-3' (SEQ ID NO:1), wherein said dye-binding step comprises contacting said 5S rRNA amplification product with a nucleic acid binding dye; and detecting the presence or absence of binding of said nucleic acid binding dye to said amplification product, wherein the presence of binding is indicative of the presence of Legion din in said sample, and wherein the absence of binding is indicative of the absence of *Legionella* in said sample.

58. The method of claim 57, wherein said second 5S rRNA primer comprises the sequence 5'-GGC GAT GAC CTA CTT TC-3' (SEQ ID NO:2).

59. A method for detecting the presence or absence of *Legionella* in a biological sample from an individual, said method comprising:

performing at least one cycling step, wherein a cycling step comprises an amplifying step and a dye-binding step, wherein said amplifying step comprises contacting said sample with a pair of 5S rRNA primers to produce a 5S rRNA amplification product if a *Legionella* 5S rRNA nucleic acid molecule is present in said sample, wherein said pair or 5S rRNA primers comprises a first 5S rRNA primer and a second 5S rRNA primer, wherein said second 5S rRNA primer comprises the sequence 5'-GGC GAT GAC CTA CTT TC-3' (SEQ ID NO:2), wherein said dye-binding step comprises contacting said 5S rRNA amplification product with a nucleic acid binding dye; and detecting the presence or absence of binding of said nucleic acid binding dye to said amplification product, wherein the presence of binding is indicative of the presence of *Legionella* in said sample, and wherein the absence of binding is indicative of the absence of *Legionella* in said sample.

60. The method of claim 59, wherein said first 5S rRNA primer comprises the sequence 5'-ACT ATA GCG ATT TGG AAC C-3' (SEQ ID NO:1).

61. A method for detecting the presence or absence of *L. pneumophila* in a biological sample from an individual, said method comprising:

performing at least one cycling step, wherein a cycling step comprises an amplifying step and a dye-binding step, wherein said amplifying step comprises contacting said sample with a pair of mip primers to produce a mip amplification product if a *L. pneumophila* mip nucleic acid molecule is present in said sample, wherein said pair of mip primers comprises a first mip primer and a second mip primer, wherein said first mip primer comprises the sequence 5'-ACC GAA CAG CAA ATG AAA GA-3' (SEQ ID NO:4), wherein said dye-binding step comprises contacting said mip amplification product with a nucleic acid binding dye; and detecting the presence or absence of binding of said nucleic acid binding dye to said amplification product, wherein the presence of binding is indicative or the presence of *L. pneumophila* in said sample, and wherein the absence of binding is indicative of the absence of *L. pneumophila* in said sample.

62. The method of claim 61, wherein said second mip primer comprises the sequence 5'-AAC GCC TGG CTT GTT TTT GT-3' (SEQ ID NO:5).

63. A method for detecting the presence or absence of *L. pneumophila* in a biological sample from an individual, said method comprising:

performing at least one cycling step, wherein a cycling step comprises an amplifying step and a dye-binding step, wherein said amplifying step comprises contacting said sample with a pair of mip primers to produce a mip amplification product if a *L. pneumophila* mip nucleic acid molecule is present in said sample, wherein said pair of mip primers comprises a first mip primer and a second mip primer, wherein said second mip primer comprises the sequence 5'-AAC GCC TGG CTT GTT TIT GT-3' (SEQ ID NO:5), wherein said dye-binding step comprises contacting said mip amplification product with a nucleic acid binding dye; and detecting the presence or absence of binding of said nucleic acid binding dye to said amplification product, wherein the presence of binding is indicative of the presence of *L. pneumophila* in said sample, and wherein the absence of binding is indicative of the absence of *L. pneumophila* in said sample.

64. The method of claim 63, wherein said first mip primer comprises the sequence 5'-ACC GAA CAG CAA ATG AAA GA-3' SEQ ID NO:4).

65. The method of claim 57, 59, 61, or 63, wherein said nucleic acid binding dye is ethidium bromide.

66. The method of claim 57, 59, 61, or 63, further comprising determining the melting temperature between said amplification product and said nucleic acid binding dye, wherein said melting temperature confirms said presence or absence of said *L. pneumophila*.

67. An article of manufacture, comprising:
a pair of 5S rRNA primers, wherein said pair of 5S rRNA primers comprises a first 5S rRNA primer and a second 5S rRNA primer, wherein said first 5S rRNA primer comprises the sequence 5'-ACT ATA GCG ATT TGG AAC C-3' (SEQ ID NO:1).

68. The article of manufacture of claim 67, wherein said second 5S rRNA primer comprises the sequence 5'-GGC GAT GAC CTA CTT TC-3' (SEQ ID NO:2).

69. An article of manufacture, comprising:
a pair of 5S rRNA primers, wherein said pair of 5S rRNA primers comprises a first 5S rRNA primer and a second 5S rRNA primer, wherein said second 5S rRNA primer comprises the sequence 5'-GGC GAT GAC CTA CTT TC-3' (SEQ ID NO:2).

70. The article of manufacture of claim 69, wherein said first 5S rRNA primer comprises the sequence 5'-ACT ATA GCG ATT TGG AAC C-3' (SEQ ID NO:1).

71. An article of manufacture, comprising
a pair of 5S rRNA probes, wherein said pair of 5S rRNA probes comprises a first 5S rRNA probe and a second 5S rRNA probe, wherein said first 5S rRNA probe comprises the sequence 5'-CAT GAG GAA GCC TCA CAC TAT CA-3' (SEQ ID NO:3).

72. The article of manufacture of claim 71, wherein said second 5S rRNA probe comprises the sequence 5'-GGC GAT GAC CTA CTT TC-3' (SEQ ID NO:2).

73. An article of manufacture, comprising
a pair of 5S rRNA probes, wherein said pair of 5S rRNA probes comprises a first 5S rRNA probe and a second 5S rRNA probe, wherein said second 5S rRNA probe comprises the sequence 5'-GGC GAT GAC CTA CTT TC3' (SEQ ID NO:2).

74. The article of manufacture of claim 73, wherein said first 5S rRNA probe comprises the sequence 5'-CAT GAG GAA GCC TCA CAC TAT CA-3' (SEQ ID NO:3).

75. The article of manufacture of claim 71 or 73, further comprising a donor fluorescent moiety and a corresponding acceptor fluorescent moiety.

76. The article of manufacture of claim 75, wherein said pair of 5S rRNA probes comprises a first 5S rRNA probe labeled with said donor fluorescent moiety and a second 5S rRNA probe labeled with said corresponding acceptor fluorescent moiety.

77. The article of manufacture of claim 67 or 69, further comprising a package label or package insert having instructions thereon for using said pair of 5S rRNA primers to detect the presence or absence of *Legionella* in a biological sample.

78. The article of manufacture of claim 71 or 73, further comprising a package label or package insert having instructions thereon for using said pair of 5S rRNA probes to detect the presence or absence of *Legionella* in a biological sample.

79. An article of manufacture comprising a pair of 5S rRNA primers and a pair of 5S rRNA probes, wherein said pair of 5S rRNA primers comprises a first 5S rRNA primer and a second 5S rRNA primer, wherein said pair of 5S rRNA probes comprises a first 5S rRNA probe and a second 5S rRNA probe, wherein said first 5S rRNA primer comprises the sequence 5'-ACT ATA GCG ATT TGG AAC C-3' (SEQ ID NO:1), wherein said second 5S rRNA primer comprises the sequence 5'-GGC GAT GAC CTA CTT TC-3' (SEQ ID NO:2), wherein said first 5S rRNA probe comprises the sequence 5'-CAT GAG GAA GCC TCA CAC TAT CA-3' (SEQ ID NO:3), wherein said second 5S rRNA probe comprises the sequence 5'-GGC GAT GAC CTA CTT TC-3' (SEQ ID NO:2).

80. An article of manufacture, comprising
a pair of mip primers, wherein said pair of mip primers comprises a first mip primer and a second mip primer, wherein said first mip primers comprises the sequence 5'-ACC GAA CAG CAA ATG AAA GA-3' (SEQ ID NO:4).

81. The article of manufacture of claim 80, comprising a second mip primer comprising the sequence 5'-AAC GCC TGG CTT GTT TTT GT-3' (SEQ ID NO:5).

82. An article of manufacture, comprising
a pair of mip primers, wherein said pair of mip primers comprises a first mip primer and a second mip primer, wherein said second mip primer comprises the sequence 5'-AAC GCC TGG CTT GTT TTT GT-3' (SEQ ID NO:5).

83. The article of manufacture of claim 82, comprising a first mip primer comprising the sequence 5'-ACC GAA CAG CAA ATG AAA GA-3' (SEQ ID NO:4).

84. An article of manufacture, comprising
a pair mip probes, wherein said pair of mip probes comprises a first mip probe and a second mip probe, wherein said first mip probe comprises the sequence 5'-AAC AAG TTT CAG AAA GAT TTG ATG GCA AAG-3' (SEQ ID NO:6).

85. The article of manufacture of claim 84, comprising a second mip probe comprising the sequence 5'-GTA CTG CTG AAT TCA ATA AGT AAG CGG ATG-3' (SEQ ID NO:7).

86. An article of manufacture, comprising
a pair of mip probes, wherein said pair of mip probes comprises a first mip probe and a second mip probe, wherein said second mip probe comprises the sequence 5'-GTA CTG CTG AAT TCA ATA AGT AAG CGG ATG-3' (SEQ ID NO:7).

87. The article of manufacture of claim 86, comprising a first mip probe comprising the sequence 5'-AAC AAG TTT CAG AAA GAT TTG ATG GCA AAG-3' (SEQ ID NO:6).

88. The article of manufacture of claim 84 or 86 further comprising a donor fluorescent moiety and a corresponding acceptor fluorescent moiety.

89. The article of manufacture of claim 88, wherein said pair of mip probes comprises a first mip probe labeled with said donor fluorescent moiety and a second mip probe labeled with said corresponding acceptor fluorescent moiety.

90. The article of manufacture of claim 80 or 82, further comprising a package label or package insert having instructions thereon for using said pair of mip primers to detect the presence or absence of *L. pneumophila* in a biological sample.

91. The article of manufacture of claim 84 or 86, further comprising a package label or package insert having instructions thereon for using said pair of mip probes to detect the presence or absence of *L. pneumophila* in a biological sample.

92. An article of manufacture comprising a pair of mip primers and a pair of mip probes, wherein said pair of mip primers comprises a first mip primer and a second mip primer, wherein said pair of mip probes comprises a first mip probe and a second mip probe, wherein said first mip primer comprises the sequence 5'-ACC GAA CAG CAA ATG AAA GA-3' (SEQ ID NO:4), wherein said second mip primer comprises the sequence 5'-AAC GCC TGG CTT GTT TTT GT-3' (SEQ ID NO:5), wherein said first mip probe comprises the sequence 5'-AAC AAG TTT CAG AAA GAT TTG ATG GCA AAG-3' (SEQ ID NO:6), wherein said second mip probe comprises the sequence 5'-GTA CTG CTG AAT TCA ATA AGT AAG CGG ATG-3' (SEQ ID NO:7).

93. An article of manufacture comprising a pair of 5S rRNA primers and a pair of 5S rRNA probes, wherein said pair of 5S rRNA primers comprises a first 5S rRNA primer and a second 5S rRNA primer, wherein said pair of 5S rRNA probes comprises a first 5S rRNA probe and a second 5S rRNA probe, wherein said first 5S rRNA primer comprises the sequence 5'-ACT ATA GCG ATT TGG AAC C-3' (SEQ ID NO:1), wherein said second 5S rRNA primer comprises the sequence 5'-GGC GAT GAC CTA CTT TC-3' (SEQ ID NO:2), wherein said first 5S rRNA probe comprises the sequence 5'-CAT GAG GAA GCC TCA CAC TAT CA-3' (SEQ ID NO:3), wherein said second 5S rRNA probe comprises the sequence 5'-GGC GAT GAC CTA CTT TC-3' (SEQ ID NO:2), said article of manufacture further comprising a pair of mip primers and a pair of mip probes, wherein said pair of mip primers comprises a first mip primer and a second mip primer, wherein said pair of mip probes comprises a first mip probe and a second mip probe, wherein said first mip primer comprises the sequence 5'-ACC GAA CAG CAA ATG AAA GA-3' (SEQ ID NO:4), wherein said second mip primer comprises the sequence 5'-AAC GCC TGG CTT GTT TTT GT-3' (SEQ ID NO:5), wherein said first mip probe comprises the sequence 5'-AAC AAG TTT CAG AAA GAT TTG ATG GCA AAG- 3' (SEQ ID NO:6), wherein said second mip probe comprises the sequence 5'-GTA CTG CTG AAT TCA ATA AGT AAG CGG ATG-3' (SEQ ID NO:7).

* * * * *

UNITED STATES PATENT AND TRADEMARK OFFICE
CERTIFICATE OF CORRECTION

PATENT NO. : 6,830,888 B2
DATED : December 14, 2004
INVENTOR(S) : Franklin R. Cockerill III et al.

It is certified that error appears in the above-identified patent and that said Letters Patent is hereby corrected as shown below:

<u>Title page,</u>
Item [56], References Cited, OTHER PUBLICATIONS, "Waterer et al." reference, please delete "Clinician'" and insert -- Clinician's -- therefor;

<u>Column 31,</u>
Line 24, please delete "as" and insert -- a -- therefor;
Line 45, please delete "an" and insert -- in -- therefor;

<u>Column 32,</u>
Line 41, please delete "hybridizing" and insert -- hybridize -- therefor;

<u>Column 33,</u>
Line 57, please delete "nip" and insert -- mip -- therefor;
Line 62, please delete "or" and insert -- of -- therefor;

<u>Column 34,</u>
Line 63, after "second" please insert -- mip --;

<u>Column 35,</u>
Line 34, please delete "staid" and insert -- said -- therefor;
Line 63, please delete "snip" and insert -- mip -- therefor;
Line 64, please delete "ACT" and insert -- AGT -- therefor;

<u>Column 36,</u>
Lines 2 and 3, please delete "snip" and insert -- mip -- therefor
Line 11, after "6" please insert -- ) --;
Line 25, please delete "snip" and insert -- mip -- therefor;

<u>Column 38,</u>
Line 42, please delete "or" and insert -- of -- therefor;

<u>Column 39,</u>
Line 62, please delete "Legion din" and insert -- Legionella -- therefor;

UNITED STATES PATENT AND TRADEMARK OFFICE
CERTIFICATE OF CORRECTION

PATENT NO. : 6,830,888 B2
DATED : December 14, 2004
INVENTOR(S) : Franklin R. Cockerill III, et al.

It is certified that error appears in the above-identified patent and that said Letters Patent is hereby corrected as shown below:

Column 40,
Line 44, please delete "or" and insert -- of -- therefor;

Column 42,
Line 33, after the first occurrence of "pair", please insert -- of --.

Signed and Sealed this

Seventh Day of June, 2005

JON W. DUDAS
*Director of the United States Patent and Trademark Office*

SEQUENCE LISTING

<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Oligonucleotides

<400> SEQUENCE: 1
actatagcga tttggaacc                    19

<210> SEQ ID NO 2
<211> LENGTH: 17
<212> TYPE: DNA
<213> ORGANISM: Artificial Sequence
<220> FEATURE:
<223> OTHER INFORMATION: Oligonucleotides

```
-continued

<400> SEQUENCE: 2
ggcgatgacc tactttc                                                17

<210> SEQ ID NO 3
<211> LENGTH: 23
<212> TYPE: DNA
<213> ORGANISM: Artificial Sequence
<220> FEATURE:
<223> OTHER INFORMATION: Oligonucleotides

<400> SEQUENCE: 3
catgaggaag cctcacacta tca                                         23

<210> SEQ ID NO 4
<211> LENGTH: 20
<212> TYPE: DNA
<213> ORGANISM: Artificial Sequence
<220> FEATURE:
<223> OTHER INFORMATION: Oligonucleotides

<400> SEQUENCE: 4
accgaacagc aaatgaaaga                                             20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotides

<400> SEQUENCE: 5
aacgcctggc ttgtttttgt                                             20

<210> SEQ ID NO 6
<211> LENGTH: 30
<212> TYPE: DNA
<213> ORGANISM: Artificial Sequence
<220> FEATURE:
<223> OTHER INFORMATION: Oligonucleotides

<400> SEQUENCE: 6
aacaagtttc agaaagattt gatggcaaag                                  30

<210> SEQ ID NO 7
<211> LENGTH: 30
<212> TYPE: DNA
<213> ORGANISM: Artificial Sequence
<220> FEATURE:
<223> OTHER INFORMATION: Oligonucleotides

<400> SEQUENCE: 7
gtactgctga attcaataag taagcggatg                                  30

<210> SEQ ID NO 8
<211> LENGTH: 18
<212> TYPE: DNA
<213> ORGANISM: Artificial Sequence
<220> FEATURE:
<223> OTHER INFORMATION: Oligonucleotides

<400> SEQUENCE: 8
atctgaccgt cccaggtt                                               18

<210> SEQ ID NO 9
<211> LENGTH: 18
```

-continued

```
<212> TYPE: DNA
<213> ORGANISM: Artificial Sequence
<220> FEATURE:
<223> OTHER INFORMATION: Oligonucleotides

<400> SEQUENCE: 9
agctttcatc caaagata                                                 18
```